(12) United States Patent
Lee et al.

(10) Patent No.: US 8,470,836 B2
(45) Date of Patent: Jun. 25, 2013

(54) DIPEPTIDYL PEPTIDASE-IV INHIBITING COMPOUNDS, METHODS OF PREPARING THE SAME, AND PHARMACEUTICAL COMPOSITIONS CONTAINING THE SAME AS ACTIVE AGENT

(75) Inventors: Chang-Seok Lee, Daejeon (KR); Hyeon Joo Yim, Daejeon (KR); Kyoung-Hee Kim, Daejeon (KR); Jaeick Lee, Daejeon (KR); Sung-Hack Lee, Daejeon (KR); Kyu Woong Lee, Daejeon (KR); Hee Bong Lee, Daejeon (KR); Wan Su Park, Daejeon (KR); Changhee Min, Daejeon (KR)

(73) Assignee: LG Life Sciences, Ltd., Seoul (KR)

( * ) Notice: Subject to any disclaimer, the term of this patent is extended or adjusted under 35 U.S.C. 154(b) by 382 days.

(21) Appl. No.: 12/747,860

(22) PCT Filed: Dec. 19, 2008

(86) PCT No.: PCT/KR2008/007543
§ 371 (c)(1),
(2), (4) Date: Jun. 11, 2010

(87) PCT Pub. No.: WO2009/082134
PCT Pub. Date: Jul. 2, 2009

(65) Prior Publication Data
US 2010/0274013 A1    Oct. 28, 2010

(30) Foreign Application Priority Data
Dec. 21, 2007 (KR) .................. 10-2007-0134887

(51) Int. Cl.
A01N 43/90    (2006.01)
A61K 31/519   (2006.01)
C07D 471/00   (2006.01)
C07D 487/00   (2006.01)

(52) U.S. Cl.
USPC ........................... 514/264.1; 544/279

(58) Field of Classification Search
USPC ........................... 514/264.1; 544/279
See application file for complete search history.

(56) References Cited

FOREIGN PATENT DOCUMENTS

| WO | 00/34241 A1 | 6/2000 |
|---|---|---|
| WO | 03004498 A1 | 1/2003 |
| WO | 03037327 A1 | 5/2003 |
| WO | 03082817 A2 | 10/2003 |
| WO | 2004064778 A2 | 8/2004 |
| WO | 2006104356 A1 | 10/2006 |
| WO | WO 2006/104356 | * 10/2006 |

OTHER PUBLICATIONS

PCT International Search Report for PCT Application No. PCT/KR2008/007543 mailed on Aug. 6, 2009.
PCT Written Opinion for PCT Application No. PCT/KR2008/007543 mailed Aug. 6, 2009.
PCT Chapter II International Preliminary Report on Patentability completed on Mar. 2, 2010.
Zimmet, Paul, et al., "Global and societal implications of the diabetes epidemic", Nature, Dec. 13, 2001, vol. 414, pp. 782-787.
Moller, David E., "New drug targets for type 2 diabetes and the metabolic syndrome", Nature, Dec. 13, 2001, vol. 414, pp. 821-827.
Marguet, Didier, et al., "Enhanced insulin secretion and improved glucose tolerance in mice lacking CD26", Proc. Natl. Acad. Sci. USA, (PNAS), Jun. 6, 2000, vol. 97, pp. 6874-6879.
Pospislik, J. A., et al., "Long-Term Treatment With the Dipeptidyl Peptidase IV Inhibitor P32/98 Causes Sustained Improvements in Glucose Tolerance, Insulin Sensitivity, Hyperinsulinemia, and β-Cell Glucose Responsiveness in VDF (ƒα/ƒα) Zucker Rats", Diabetes, Apr. 2002, vol. 51, pp. 943-950.
Lankas, George R., et al., "Potential Importance of Selectivity over Dipeptidyl Peptidases 8 and 9", Dipeptidyl Peptidase IV Inhibition for the Treatment of Type 2 Diabetes, American Diabetes Association, Oct. 2005, vol. 54, pp. 2988-2994.
Tanaka, Toshiaki, et al, "Enhancement of antigen-induced T-cell proliferation by soluble CD26/dipeptidyl peptidase IV", Proc. Natl. Acad. Sci. USA, Apr. 1994, vol. 91, pp. 3082-3086.
Dooseop Kim, et al., "(2R)-4-Oxo-4-[3-(Trifluoromethyl)-5,6-dihydro[1,2,4]triazolo[4,3-α]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes", Journal of Medicinal Chemistry, 2005, vol. 48, No. 1, pp. 141-151.

* cited by examiner

Primary Examiner — Erich A Leeser
(74) Attorney, Agent, or Firm — Ladas & Parry, LLP

(57) ABSTRACT

Disclosed herein are novel compounds of Formula (1) as defined in the specification having excellent inhibitory activity against dipeptidyl peptidase-IV (DPP-IV), methods of preparing the same and pharmaceutical compositions comprising the same as an active agent.

12 Claims, No Drawings

DIPEPTIDYL PEPTIDASE-IV INHIBITING COMPOUNDS, METHODS OF PREPARING THE SAME, AND PHARMACEUTICAL COMPOSITIONS CONTAINING THE SAME AS ACTIVE AGENT

CROSS-REFERENCE TO RELATED APPLICATIONS

This application is the U.S. National Stage of International Patent Application No. PCT/KR2008/007543, filed on Dec. 19, 2008, which claims priority to Korean Patent Application No. 10-2007-0134887 filed on Dec. 21, 2007, the disclosures of which are incorporated herein by reference.

FIELD OF THE INVENTION

The present invention relates to novel compounds having excellent inhibitory activity against dipeptidyl peptidase-IV (DPP-IV), methods of preparing the same and pharmaceutical compositions comprising the same as an active agent.

BACKGROUND OF THE INVENTION

Diabetes has significant adverse serious effects on human health and accompanies various complications. There are two major types of diabetes: type I diabetes mellitus characterized by little or no insulin secretory capacity due to the destruction of pancreatic cells, and type II diabetes mellitus characterized by insulin deficiency and insulin resistance due to other causes. The incidence of type II diabetes mellitus accounts for 90% or more of total diabetic patients. Representative examples of diabetic complications include hyperlipidemia, hypertension, retinopathy and renal insufficiency (Paul Zimmer, et al., Nature, 2001, 414, 782). Sulfonylureas (stimulation of pancreatic insulin secretion), biguanides (inhibition of hepatic glucose production), α-glucosidase inhibitors (suppression of intestinal glucose absorption), etc. have been used as antidiabetic agents. Recently, peroxisome proliferator-activated receptor gamma (PPARγ) agonists (thiazolidinediones, promotion of insulin sensitivity) are drawing a great deal of attention as promising antidiabetic therapeutics. However, these antidiabetic drugs have adverse side effects such as hypoglycemia, weight gain and the like (David E. Moller, Nature, 2001, 414, 821). To this end, there is an urgent need for development of diabetes therapeutics with decreased side effects, in particular without causing hypoglycemia and weight gain.

Meanwhile, it has recently been found that dipeptidyl peptidase-IV (DPP-IV) knockout mice maintains glucagon-like protein 1 (GLP-1) activity and high insulin levels, resulting in decreased blood glucose levels, suggesting the therapeutic feasibility of DPP-IV as an antidiabetic agent (Marguet D. et al, Natl. Acad. Sci. USA, (2000) 97, 6874-6879). GLP-1 is involved in the differentiation and growth of pancreatic β-cells in vivo and plays an important role in the production and secretion of insulin. GLP-1 is inactivated by DPP-IV, and DPP-IV inhibitors have been reported to increase insulin secretion via the inhibition of GLP-1 inactivation. DPP-IV inhibitors are also being developed as anti-obesity drugs because GLP-1 contributes to satiety and fullness in rats and slows down intestinal digestion of food, resulting in weight loss. Further, many researchers and institutions have also demonstrated that DPP-IV inhibitors control blood glucose and lipid levels in animal model experiments (Pospislik J. A., et al, Diabetes, (2002) 51, 943-950). In this regard, DPP-IV inhibitors can be considered as potentially useful agents for the treatment of diabetic diseases.

To date, much research for finding and developing beneficial DPP-IV inhibitors has focused on materials in which a cyano group is introduced to a pyrrolidine ring. For example, WO 00/34241 discloses DPP-IV inhibitors represented by the following formula.

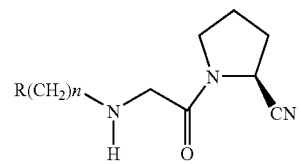

wherein R is substituted adamantyl, and n is in a range of 0 to 3.

Other inhibitors can be found in WO 04/064778, WO 03/004498, WO 03/082817, and the like. Disclosed in WO 04/064778 DPP-IV are DPP-IV inhibitors represented by the following formula.

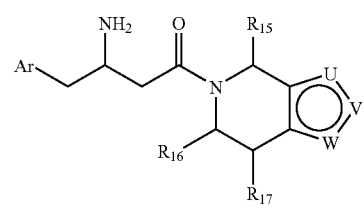

wherein Ar is unsubstituted or substituted phenyl; $R_{15}$, $R_{16}$ and $R_{17}$ are each independently hydrogen or alkyl; and U, V and W are each independently nitrogen, oxygen, or substituted nitrogen or carbon.

In addition, WO 03/004498 suggests DPP-IV inhibitors represented by the following formula.

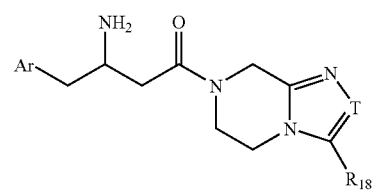

wherein Ar is unsubstituted or substituted phenyl; $R_{18}$ is hydrogen or alkyl; and T is nitrogen or substituted carbon.

Further, WO 03/082817 discloses DPP-IV inhibitors represented by the following formula.

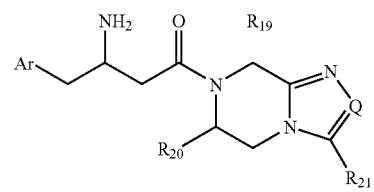

wherein Ar is unsubstituted or substituted phenyl; $R_{19}$, $R_{20}$ and $R_{21}$ are each independently hydrogen or alkyl; and Q is nitrogen or substituted carbon.

In a DPP-IV inhibitor-related patent publication WO 06/104356 assigned to the present applicant and entitled "DIPEPTIDYL PEPTIDASE-IV INHIBITING COMPOUNDS", the present inventors have demonstrated extensive and comprehensive effects of compounds represented by Formula I' below.

The compounds of Formula I' are cyclic compounds having rings connected via an amide bond, which are similar to those of DPP-IV inhibitor compounds set forth in the above-mentioned patent publications; however, the molecular structures substituted with a phenyl group, which is represented as Ar or Z in the above documents, are completely different from the structures substituted with a saturated or unsaturated, 5-membered or 6-membered cyclic moiety as in the present invention. Further, to the best of our knowledge, there is yet no disclosure in the art of DPP-IV inhibitors according to the present invention, having the molecular structure where a lactam ring is substituted at the phenyl position.

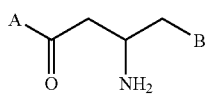

(1')

Further, the inventors of the present invention discovered that the compounds of Formula I' disclosed in the prior patent of the present applicant can exhibit significantly improved inhibitory activity and selectivity for DPP-IV through the introduction of amines having high DPP-IV inhibitory effects into substituent A and the introduction of various substituents (such as hydroxy or carbonyl group) into substituent B.

In particular, taking into consideration recent reports demonstrating that low selectivity of the conventional art for other dipeptidyl peptidases may result in a variety of adverse effects (Lankas, G. R. et al., Potential Importance of Selectivity over Dipeptidyl Peptidases 8 and 9, diabetes, 2005, 548, 2988-1994), the present invention provides highly significant results in terms of excellent pharmaceutical efficacy and high DPP-IV selectivity of the inventive compounds. Moreover, DPP-IV inhibitor compounds of the present invention having the aforementioned chemical structure and preparation methods thereof have not been disclosed in the related art.

SUMMARY OF THE INVENTION

As a result of a variety of extensive and intensive studies and experiments to solve the problems as described above and to find compounds having superior DPP-IV inhibitory activity and selectivity, the inventors of the present invention have discovered, as will be illustrated hereinafter, that compounds having an optionally substituted lactam ring structure are effective as DPP-IV inhibitors. The present invention has been completed based on these findings.

It is therefore an object of the invention to provide DPP-IV inhibitor compounds having a lactam ring structure which is optionally substituted, particularly by hydroxy or carbonyl.

It is another object of the present invention to provide methods for preparation of the same compounds.

It is a further object of the present invention to provide pharmaceutical compositions comprising the same compounds, and methods for treating or preventing DPP-IV-related diseases, comprising administering an effective amount of the same compounds to a subject in need thereof.

In accordance with an aspect of the present invention, the above and other objects can be accomplished by the provision of a dipeptidyl peptidase-IV (DPP-IV) inhibitor compound represented by Formula 1:

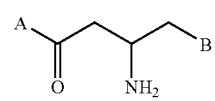

(1)

wherein

A is selected from a substituent of Formula 2:

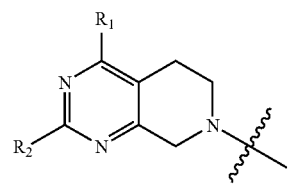

(2)

wherein $R_1$ is hydrogen or $CF_3$, and $R_2$ is selected from the group consisting of hydrogen, substituted or unsubstituted $C_1$-$C_{10}$ alkyl, substituted or unsubstituted $C_3$-$C_{10}$ cycloalkyl, substituted or unsubstituted $C_4$-$C_8$ aryl and substituted or unsubstituted $C_3$-$C_7$ heteroaryl; and a substituent of Formula 3:

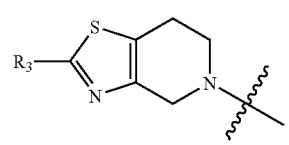

(3)

wherein $R_3$ is selected from the group consisting of hydrogen, halogen, and substituted or unsubstituted $C_1$-$C_4$ alkyl; and B is selected from the group consisting of a substituent of Formula 4:

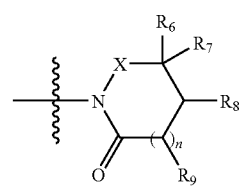

(4)

wherein

X is —$CR_4R_5$— or —CO—, wherein $R_4$ and $R_5$ are each independently hydrogen or hydroxy, provided that at least one of $R_4$ and $R_5$ is hydroxy, $R_6$, $R_7$, $R_8$ and $R_9$ are each independently selected from the group consisting of hydrogen, halogen and substituted or unsubstituted $C_1$-$C_4$ alkyl, and n is 0 or 1;

a substituent of Formula 5:

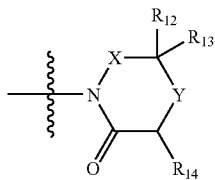

(5)

wherein

X is —CR$_{10}$R$_{11}$— or —CO—, wherein R$_{10}$ and R$_{11}$ are each independently hydrogen or hydroxy, provided that at least one of R$_{10}$ and R$_{11}$ is hydroxy, R$_{12}$, R$_{13}$ and R$_{14}$ are each independently selected from the group consisting of hydrogen, halogen and substituted or unsubstituted C$_1$-C$_4$ alkyl, and Y is oxygen or sulfur;

a substituent of Formula 6:

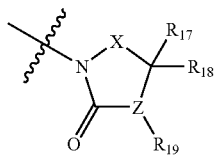

(6)

wherein

X is —CR$_{15}$R$_{16}$— or —CO—, wherein R$_{15}$ and R$_{16}$ are each independently hydrogen or hydroxy, provided that at least one of R$_{15}$ and R$_{16}$ is hydroxy, R$_{17}$, R$_{18}$ and R$_{19}$ are each independently selected from the group consisting of hydrogen, halogen, and substituted or unsubstituted C$_1$-C$_4$ alkyl, and Z is —CH— or oxygen, provided that when Z is oxygen, R$_{19}$ is absent; and a substituent of Formula 7:

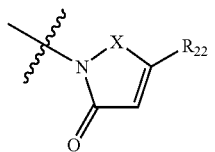

(7)

wherein

X is —CR$_{20}$R$_{21}$— or —CO—, wherein R$_{20}$ and R$_{21}$ are each independently hydrogen or hydroxy, provided that at least one of R$_{20}$ and R$_{21}$ is hydroxy, and R$_{22}$ is substituted or unsubstituted C$_1$-C$_4$ alkyl.

According to various experiments conducted by the inventors of the present invention, it was confirmed that compounds of Formula 1 exhibit significant improvements in DPP-IV inhibitory activity and selectivity through the introduction of amine groups having excellent DPP-IV inhibitory effects into substituent A and the introduction of a certain substituent group (such as hydroxy or carbonyl group) as substituent B into the existing ring structure.

Further, compounds of the present invention can form addition salts with pharmaceutically acceptable acids.

The term "pharmaceutically acceptable salt" means a formulation of a compound that does not cause significant irritation to an organism to which it is administered and does not abrogate the biological activity and properties of the compound. Examples of the pharmaceutical salt may include acid addition salts of the compound with acids capable of forming a non-toxic acid addition salt containing pharmaceutically acceptable anions, for example, inorganic acids such as hydrochloric acid, sulfuric acid, nitric acid, phosphoric acid, hydrobromic acid and hydroiodic acid; organic carboxylic acids such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acids such as methanesulfonic acid, ethanesulfonic acid, benzenesulfonic acid and p-toluenesulfonic acid. Specifically, examples of pharmaceutically acceptable carboxylic acid salts include salts with alkali metals or alkaline earth metals such as lithium, sodium, potassium, calcium and magnesium, salts with amino acids such as lysine, arginine and guanidine, and salts with organic bases such as dicyclohexylamine, N-methyl-D-glucamine, tris(hydroxymethyl)methylamine, diethanolamine, choline and triethylamine. The compound of Formula 1 in accordance with the present invention may be converted into a salt thereof, by conventional methods known in the art.

Unless otherwise indicated, the term "compound of Formula 1" is intended to encompass compounds of Formula 1 per se as well as pharmaceutically acceptable salts.

As used herein, the term "alkyl" means a radical that has no unsaturated group and consists of carbon and hydrogen atoms. The alkyl radical may be linear or branched. Examples of alkyl may include, but are not limited to, methyl, ethyl, propyl, isopropyl, hexyl, t-butyl, and sec-butyl.

Lower alkyl is C$_1$-C$_{10}$ alkyl (for example, alkyl having 1 to 10 carbon atoms in a linear or branched alkyl backbone). The alkyl may be optionally substituted. When it is substituted, the alkyl may be substituted by four or less substituents at any binding point (any carbon atom).

When the alkyl is substituted with another alkyl, this is also intended to refer to "branched alkyl".

As used herein, the term "cycloalkyl" refers to an alkyl species that contains 3 to 15 carbon atoms, preferably 3 to 8 carbon atoms, without the formation of alternate or resonant double bond(s) between the carbon atoms. The cycloalkyl may contain 1 to 4 rings. Examples of the cycloalkyl may include cyclopropyl, cyclobutyl, cyclopentyl, cyclohexyl, and adamantyl. Exemplary substituents of the cycloalkyl may include halogen, C$_1$-C$_{10}$ alkyl, C$_1$-C$_{10}$ alkoxy, C$_1$-C$_{10}$ alkyl hydroxy, amino, nitro, cyano, thiol and C$_1$-C$_{10}$ alkylthio.

Heterocycloalkyl are saturated or unsaturated, 7 to 11-membered bicyclic heterocyclic ring systems or stable non-aromatic 3 to 8-membered monocyclic heterocyclic ring systems, or may be fused, spiro, or bridged ring systems, wherein ring carbons are substituted with hetero atoms such as nitrogen (N), sulfur (S) or oxygen (O). Each heterocyclic ring consists of one or more carbon atoms and 1 to 4 hetero atoms. The heterocycloalkyl may be attached at any endocyclic carbon atom that results in a stable structure. Preferred examples of the heterocyclic groups may include, but are not limited to, furan, thiophene, pyrrole, pyrroline, pyrrolidine, oxazole, thiazole, imidazole, imidazoline, imidazolidine, pyrazole, pyrazoline, pyrazolidine, isothiazole, triazole, thiadiazole, pyran, pyridine, piperidine, morpholine, thiomorpholine, pyridazine, pyrimidine, pyrazine, piperazine and triazine. Examples of the heterocyclic rings may include, but are not limited to, 3 to 7-membered monocyclic heterocyclic rings such as piperidinyl, pyranyl, piperazinyl, morpholinyl, thiomorpholinyl and tetrahydrofuranyl, and more preferably 3 to 7-membered monocyclic heterocyclic rings.

The term "aryl" refers to an aromatic group which has at least one ring having a conjugated pi (π) electron system and includes carbocyclic aryl (for example, phenyl) and heterocyclic aryl (for example, pyridine) groups. This term is intended to include monocyclic or fused-ring polycyclic (i.e., rings which share adjacent pairs of carbon atoms) groups. The aryl group may optionally contain 1 to 4 hetero atoms (for example, nitrogen (N), sulfur (S) or oxygen (O)) in a carbocyclic or aromatic ring, and such a hetero atom-containing aryl system is also referred to as "heteroaryl".

Examples of aryl or heteroaryl groups may include, but are not limited to, phenyl, naphthyl, pyridyl, pyrimidyl, pyrrolyl, isothiazolyl, triazolyl, tetrazolyl, pyrazolyl, oxazolyl, isoxazolyl, pyrazinyl, pyridazinyl, triazinyl, quinazolinyl, thiazolyl, benzothiophenyl, furanyl, imidazolyl and thiophenyl.

In the compound of Formula 1 in accordance with the present invention, when alkyl, cycloalkyl, heterocycloalkyl, aryl or heteroaryl is substituted, the substituent may be $C_1$-$C_{10}$ alkyl or halogen, particularly preferably fluorine-substituted $C_1$-$C_{10}$ alkyl.

In one preferred embodiment of the present invention, A in Formula 1 is a substituent represented by Formula 2 wherein $R_1$ is hydrogen or $CF_3$, and $R_2$ is selected from the group consisting of hydrogen, and $C_1$-$C_5$ alkyl, $C_3$-$C_6$ cycloalkyl, $C_3$-$C_{10}$ heterocycloalkyl, $C_4$-$C_8$ aryl and $C_3$-$C_7$ heteroaryl, each of which may be optionally substituted by halogen.

When $R_2$ is unsubstituted or halogen-substituted $C_3$-$C_{10}$ heterocycloalkyl or unsubstituted or halogen-substituted $C_3$-$C_7$ heteroaryl, the heterocycloalkyl or heteroaryl may be any one selected from the group consisting of furan, thiophene, pyrrole, pyrrolidine, imidazole, pyrazole, pyrazoline, oxazole, oxazoline, isoxazole, isoxazoline, thiazole, thiazoline, isothiazole, isothiazolidine, thiadiazole, thiadiazoline, tetrahydrofuran, tetrahydrothiophene, imidazolidine, pyrazolidine, oxazolidine, isoxazolidine, thiazolidine, isothiazolidine, thiadiazolidine, sulfolane, pyran, dihydropyran, tetrahydropyran, pyridine, pyridinone, pyridazine, pyrazine, pyrimidine, piperidine, piperazine, morpholine, pyridazinone, tetrazole, triazole, triazolidine and azepine.

In a more preferred embodiment of the present invention, $R_2$ may be selected from the group consisting of trifluoromethyl, propyl, butyl, t-butyl, cyclobutyl, pyridine, furan, methoxyethyl, thiophene and 4-fluorophenyl.

Further, B in Formula 1 is a substituent represented by Formula 4 wherein X is —(CH—OH)— or —CO—, $R_6$ and $R_7$ are each independently selected from the group consisting of hydrogen, fluoro and unsubstituted $C_1$-$C_4$ alkyl, and $R_8$ and $R_9$ are each independently hydrogen.

The compounds of the present invention encompass their isomers. Particularly preferred are compounds where an $NH_2$-substituted carbon atom forms a stereogenic center, as shown in a structure of Formula 1a.

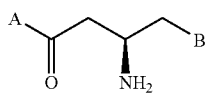

(1a)

wherein A and B are as defined for Formula 1.

Particularly preferably, non-limiting examples of the compounds of Formula 1 in accordance with the present invention may include the following compounds:

1-[(2S)-amino-4-(2,4-bis-trifluoromethyl-5,8-dihydro-6H-pyrido[3,4-d]pyrimidin-7-yl)-4-oxo-butyl]-5,5-difluoro-(6R)-hydroxy-piperidin-2-one, 1-[(2S)-amino-4-(2,4-bis-trifluoromethyl-5,8-dihydro-6H-pyrido[3,4-d]pyrimidin-7-yl)-4-oxo-butyl]-5,5-difluoro-(6S)-hydroxy-piperidin-2-one, 1-[(S)-2-amino-4-oxo-4-(2-propyl-4-trifluoromethyl-5,8-dihydro-6H-pyrido[3,4-d]pyrimidin-7-yl)-butyl]-5,5-difluoro-6-hydroxy-piperidin-2-one, 1-[(S)-2-amino-4-(2-t-butyl-4-trifluoromethyl-5,8-dihydro-6H-pyrido[3,4-d]pyrimidin-7-yl)-4-oxo-butyl]-5,5-difluoro-6-hydroxy-piperidin-2-one, 1-[(S)-2-amino-4-(2-cyclobutyl-4-trifluoromethyl-5,8-dihydro-6H-pyrido[3,4-d]pyrimidin-7-yl)-4-oxo-butyl]-5,5-difluoro-6-hydroxy-piperidin-2-one, 1-[(S)-2-amino-4-oxo-4-(2-pyridin-4-yl-4-trifluoromethyl-5,8-dihydro-6H-pyrido[3,4-d]pyrimidin-7-yl)-butyl]-5,5-difluoro-6-hydroxy-piperidin-2-one, 1-[(S)-2-amino-4-oxo-4-(2-pyridin-4-yl-4-trifluoromethyl-5,8-dihydro-6H-pyrido[3,4-d]pyrimidin-7-yl)-butyl]-5,5-difluoro-6-hydroxy-piperidin-2-one, 1-[(S)-2-amino-4-(2-furan-2-yl-4-trifluoromethyl-5,8-dihydro-6H-pyrido[3,4-d]pyrimidin-7-yl)-butyl]-4-oxo-butyl]-5,5-difluoro-6-hydroxy-piperidin-2-one, 1-[(S)-2-amino-4-(2-furan-2-yl-4-trifluoromethyl-5,8-dihydro-6H-pyrido[3,4-d]pyrimidin-7-yl)-butyl]-4-oxo-butyl]-5,5-difluoro-6-hydroxy-piperidin-2-one, 1-{(S)-2-amino-4-[2-(2-methoxy-ethyl)-4-trifluoromethyl-5,8-dihydro-6H-pyrido[3,4-d]pyrimidin-7-yl]-4-oxo-butyl}-5,5-difluoro-6-hydroxy-piperidin-2-one, 1-{(S)-2-amino-4-[2-(2-methoxy-ethyl)-4-trifluoromethyl-5,8-dihydro-6H-pyrido[3,4-d]pyrimidin-7-yl]-4-oxo-butyl}-5,5-difluoro-6-hydroxy-piperidin-2-one, 1-[(S)-2-amino-4-oxo-4-(2-thiophen-3-yl-4-trifluoromethyl-5,8-dihydro-6H-pyrido[3,4-d]pyrimidin-7-yl)-butyl]-5,5-difluoro-6-hydroxy-piperidin-2-one, 1-[(S)-2-amino-4-oxo-4-(2-thiophen-3-yl-4-trifluoromethyl-5,8-dihydro-6H-pyrido[3,4-d]pyrimidin-7-yl)-butyl]-5,5-difluoro-6-hydroxy-piperidin-2-one, 1-{(S)-2-amino-4-[2-(4-fluoro-phenyl)-4-trifluoromethyl-5,8-dihydro-6H-pyrido[3,4-d]pyrimidin-7-yl]-4-oxo-butyl}-5,5-difluoro-6-hydroxy-piperidin-2-one, 1-[(S)-2-amino-4-(2,4-bis-trifluoromethyl-5,8-dihydro-6H-pyrido[3,4-d]pyrimidin-7-yl)-4-oxo-butyl]-3,3-difluoro-piperidine-2,6-dione, 1-[(S)-2-amino-4-(2-t-butyl-4-trifluoromethyl-5,8-dihydro-6H-pyrido[3,4-d]pyrimidin-7-yl)-4-oxo-butyl]-5-fluoro-6-hydroxy-piperidin-2-one, 1-[(S)-2-amino-4-(2-furan-2-yl-4-trifluoromethyl-5,8-dihydro-6H-pyrido[3,4-d]pyrimidin-7-yl)-4-oxo-butyl]-5-fluoro-6-hydroxy-piperidin-2-one, 1-[(S)-2-amino-4-oxo-4-(2-thiophen-3-yl-4-trifluoromethyl-5,8-dihydro-6H-pyrido[3,4-d]pyrimidin-7-yl)-butyl]-5-fluoro-6-hydroxy-piperidin-2-one, 1-[(S)-2-amino-4-oxo-4-(2-propyl-5-trifluoromethyl-5,8-dihydro-6H-pyrido[3,4-d]pyrimidin-7-yl)-butyl]-5-fluoro-6-hydroxy-piperidin-2-one, 1-[(S)-2-amino-4-oxo-4-(2-pyridin-4-yl-5-trifluoromethyl-5,8-dihydro-6H-pyrido[3,4-d]pyrimidin-7-yl)-butyl]-5-fluoro-6-hydroxy-piperidin-2-one, 1-[(S)-2-amino-4-oxo-4-(2-thiophen-3-yl-4-trifluoromethyl-5,8-dihydro-6H-pyrido[3,4-d]pyrimidin-7-yl)-butyl]-3-methyl-piperidine-2,6-dione, and 1-[(S)-2-amino-4-(2-t-butyl-4-trifluoromethyl-5,8-dihydro-6H-pyrido[3,4-d]pyrimidin-7-yl)-4-oxo-butyl]-3-methyl-pyrrolidine-2,6-dione.

The compounds of the present invention or their pharmaceutically acceptable salts may be in the form of hydrates or solvates.

Further, the present invention provides a method for preparing the compounds of Formula 1.

An exemplary method of preparing the compounds of Formula 1 comprises reacting a compound of Formula 8 with a compound of Formula 9 and removing an amine protecting group $P_1$.

$AH_2F_1$ (9)

In Formulae 8 and 9,

A and B are as defined above;

$P_1$ is an amine protecting group; and $F_1$ is absent or is hydrochloric acid, sulfuric acid or trifluoroacetic acid.

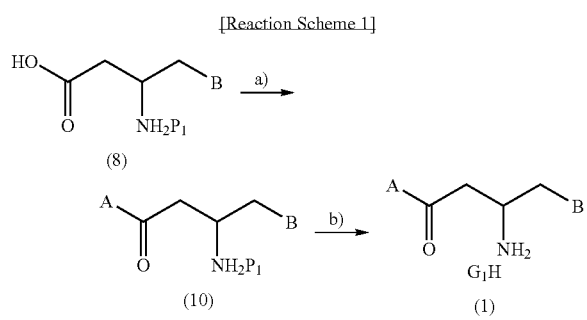

In Reaction Scheme 1, A, B and $P_1$ are as defined above; and $G_1H$ is hydrochloric acid, sulfuric acid, or trifluoroacetic acid.

Reagents and Reaction Conditions a: EDCI, HOBT, $Et_3N$ or $AH_2G_1H$ b: $G_1H$

Specifically, compound 1 can be obtained as follows. First, the desired amine group is introduced into a compound of Formula 8 via a coupling reaction using EDC and HOBT, thereby forming compound 10 as an amide. Then, the amine protecting group $P_1$ is removed to obtain compound 1, using a strong acid such as TFA or HCl when the amine protecting group $P_1$ is Boc, or $H_2$/Pd/C or TMSI using when the amine protecting group $P_1$ is Cbz, or using $Et_2NH$ when the amine protecting group $P_1$ is Fmoc.

In the reaction step a), amine A may be obtained by using methods disclosed in WO 04/064778, WO 03/004498, WO 03/082817, WO 06/104356, etc., or otherwise may be commercially available amine.

Meanwhile, the compound of Formula 8 can be prepared typically by Reaction Scheme 2 below.

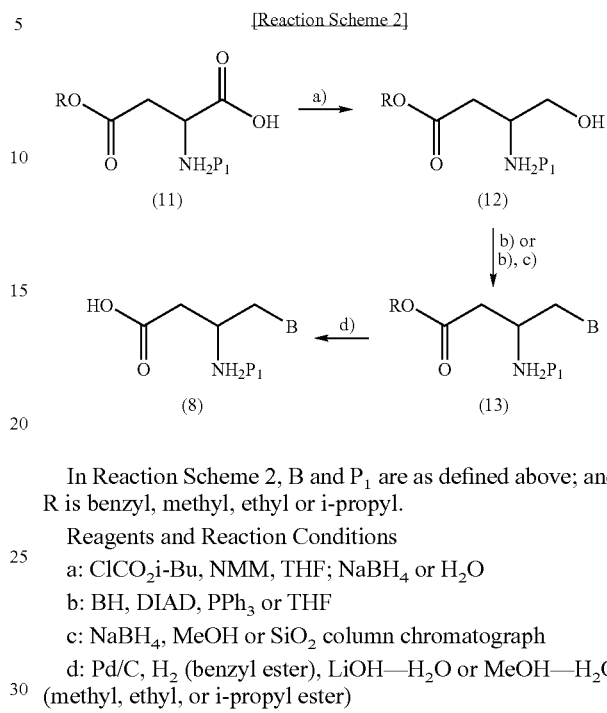

In Reaction Scheme 2, B and $P_1$ are as defined above; and R is benzyl, methyl, ethyl or i-propyl.

Reagents and Reaction Conditions a: $ClCO_2$i-Bu, NMM, THF; $NaBH_4$ or $H_2O$ b: BH, DIAD, $PPh_3$ or THF c: $NaBH_4$, MeOH or $SiO_2$ column chromatograph d: Pd/C, $H_2$ (benzyl ester), LiOH—$H_2O$ or MeOH—$H_2O$ (methyl, ethyl, or i-propyl ester)

Specifically, a carboxylic acid of Formula 11 is converted into an anhydrous ester, and the ester compound is then reduced in methanol using sodium borohydride ($NaBH_4$) to thereby obtain compound 12 as a primary alcohol. The coupling product of the resulting primary alcohol and the desired imide compound, i.e. compound 13 can be obtained using DIAD and $PPh_3$. Then, the amine protecting group $P_1$ is removed to obtain compound 8, using a strong acid such as TFA or HCl when the amine protecting group $P_1$ is Boc, or using $H_2$/Pd/C or TMSI when the amine protecting group $P_1$ is Cbz, or using $Et_2NH$ when the amine protecting group $P_1$ is Fmoc.

Meanwhile, substituent B in Formula 8 can be prepared typically according to Reaction Scheme 3-1 or Reaction Scheme 3-2 below.

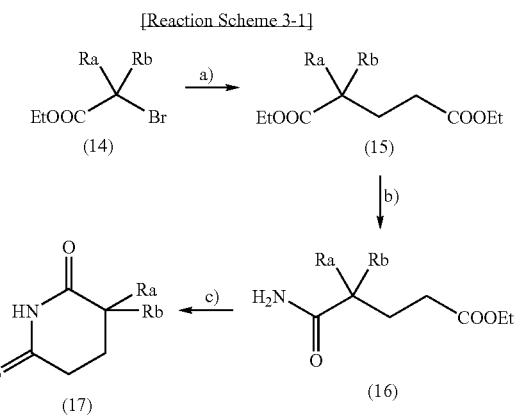

In Reaction Scheme 3-1, Ra and Rb are each independently hydrogen or halogen.

Reagents and Reaction Conditions
a: ethyl acrylate, Cu powder, TMEDA, THF
b: NH₃ in MeOH
c: NaOEt, EtOH; HCl Specifically, a diester compound of Formula 14 is obtained via the Michael addition reaction of a compound of Formula 14 with ethyl acrylate, and a compound of Formula 16 containing an amide group is obtained via the reaction of the resulting diester with ammonia. As can be seen, the reaction proceeds toward a carbonyl group adjacent to halogen, among two esters, due to the electron attraction of one or more halogen atoms contained in the reactant compound. Finally, cyclization is carried out in ethanol in the presence of sodium ethoxide to give a salt compound having sodium attached to a nitrogen atom of an imide. Treatment of the salt compound with an anhydrous strong acid provides the desired imide compound of Formula 17. The resulting insoluble NaCl solid was removed by simple filtration.

[Reaction Scheme 3-2]

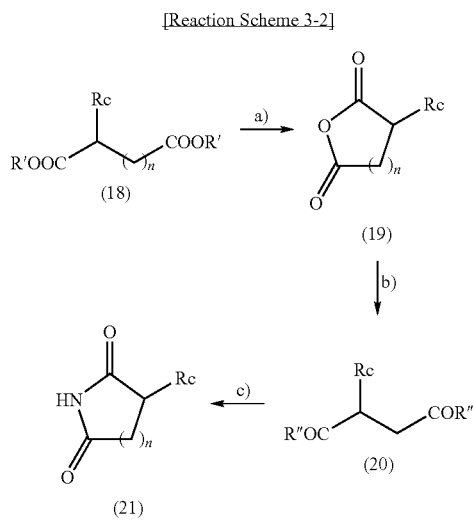

In Reaction Scheme 3-2, n is 0 or 1; R' is methyl or hydrogen; R" is hydroxy or amino; and Rc is $C_1$-$C_a$ alkyl.

Reagents and Reaction Conditions
a: Ac₂O
b: NH₄OH, THF
c: Ac₂O

If R' is methyl, the product compound is then hydrolyzed by reaction with a strong base such as lithium hydroxide or potassium hydroxide, prior to use.

Addition of an acetic anhydride as a solvent and a reactant to the diacid compound of Formula 18 results in the formation of a highly reactive intermediate in the form of an anhydride ring. A compound of Formula 20 is produced by the ring-opening of the intermediate with ammonia. Due to the absence of a strong electron-attracting substituent group unlike in Reaction Scheme 3-1, ammonia can attack carbon atoms of both ketones and therefore two types of amino acid compounds are produced. These amino acid compounds are not detrimental to the subsequent reaction and can therefore be directly used without further separation. Finally, the desired imide compound of Formula 21 is obtained via the cyclization of compound 20 in the form of amino acid by addition of an acetic anhydride as shown in Step (a).

Unless otherwise stated, starting compounds used in the present invention are known in the art or can be synthesized from known compounds by per se known methods or similar methods thereof.

The compounds of Formula 1 can be isolated and purified from the reaction product by means of conventional methods such as recrystallization, ion electrophoresis, silica gel column chromatography or ion exchange resin chromatography and the like.

As described above, the compounds according to the present invention, starting materials for the preparation thereof and intermediates can be synthesized by various methods, thus those methods should be interpreted to be included within the scope of the present invention in view of the preparation of the compounds of Formula 1.

Further, the present invention provides a pharmaceutical composition for inhibiting DPP-IV, comprising a compound of Formula 1 or a pharmaceutically acceptable salt thereof.

The pharmaceutical composition may contain a compound of the present invention and other chemical components such as diluents, carriers, and the like. Therefore, the pharmaceutical composition may contain a pharmaceutically acceptable carrier, diluent or excipient, or any combination thereof, if necessary. The pharmaceutical composition facilitates in vivo administration of the compound to a subject organism. Various techniques of administering the compound are known in the art and include, but are not limited to, oral, injection, aerosol, parenteral and topical administrations.

The term "carrier" means a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines a chemical compound diluted in water that will dissolve a composition of interest as well as stabilize the biologically active form of the composition. Salts dissolved in buffered solutions are utilized as diluents in the art. One commonly used buffer solution is phosphate buffered saline (PBS) because it mimics the salt conditions of human body fluid. Since buffer salts can control the pH of a solution at low concentrations, a buffer diluent rarely modifies the biological activity of a compound.

The term "physiologically acceptable" defines a carrier or diluent that is not detrimental to the biological activity and physical properties of the compound.

The compound of the present invention can be formulated into various pharmaceutical dosage forms in accordance with intended use. In the preparation of pharmaceutical compositions in accordance with the present invention, an active agent, more specifically a compound of Formula 1 or a pharmaceutically acceptable salt thereof may be mixed with one or more pharmaceutically acceptable carriers which can be selected depending on the dosage form to be prepared. For example, the pharmaceutical composition according to the present invention can be formulated into dosage forms suitable for injection or oral administration.

The compounds of the present invention may be formulated in a conventional manner using known pharmaceutically acceptable carriers and excipients and presented in unit dosage forms or in multidose containers. The formulations may take such forms as solutions, suspensions or emulsions in oily or aqueous vehicles, and may contain conventional dispersing, suspending or stabilizing agents. Alternatively, the active agent may be in powder form for reconstitution with sterile pyrogen-free water, before use. The compounds of the present invention may also be formulated into suppositories containing conventional suppository bases such as cocoa butter or other glycerides. Solid dosage forms for oral administration include capsules, tablets, pills, powders and granules. Preferable dosage forms are capsules and tablets. It is preferable that tablets and pills be coated. The solid dosage forms for oral administration may be obtained by mixing the compound of the present invention as an active agent with one or more inert diluents such as sucrose, lactose, starch and the like and carriers such as lubricants (for example magnesium stearate), disintegrators, binders and the like.

If necessary, the compounds of the present invention and compositions comprising the same may be administered in combination with other pharmaceutical agents, for example, other antidiabetic agents.

When the formulation is presented in unit dosage form, the compound of Formula 1 as an active agent can be preferably contained in a unit dosage of about 0. 1 to 1500 mg. The dosage amount of the compound of Formula 1 will be dependent on the subject's weight and age, the nature and severity of the affliction and the judgment of the prescribing physician. For adult administration, the dosage amount required will be in the range of 1 to 500 mg a day depending on the frequency and strength of the dosage. For intramuscular or intravenous administration to adults, a total dosage amount of about 5 to 300 mg a day will be sufficient. In some patients, the daily dosage will be higher than that.

The present invention provides methods for treating or preventing diseases involving inappropriate activity of DPP-IV by the use of effective amounts of the compounds of Formula 1. Representative examples of DPP-IV-related diseases include, but are in no way limited to, diabetes, obesity and the like as described above. Inter alia, the present invention is preferred to treat and prevent type II diabetes mellitus. The term "treating" means ceasing or delaying progress of diseases when the compounds of Formula 1 or compositions comprising the same are administered to subjects exhibiting symptoms of diseases. The term "preventing" means ceasing or delaying symptoms of diseases when the compounds of Formula 1 or compositions comprising the same are administered to subjects exhibiting no symptoms of diseases, but having high risk of developing symptoms of diseases.

DETAILED DESCRIPTION OF PREFERRED EMBODIMENTS

Now, the present invention will be described in more detail with reference to the following Examples. These examples are provided only for illustrating the present invention and should not be construed as limiting the scope and spirit of the present invention.

PREPARATION EXAMPLE 1

Synthesis of 2,4-bis-trifluoromethyl-5,6,7,8-tetrahydropyrido[3,4-d]pyrimidine hydrochloride (1) Synthesis of 3-hydroxy-piperidine-1-carboxylic acid t-butyl ester 1.0 equivalent of dibutyl dicarbonate (159 g) in 200 mL of methylene chloride were slowly added to a mixture of 3-hydroxy piperidine hydrochloride (100 g, 0.73 mol) and 1.1 equivalents of triethylamine (111 mL) in methylene chloride (800 mL) at room temperature. Then, the resulting mixture was stirred additionally for 2 hours. After the reaction was complete, the reaction solution was washed with a 1.0 N hydrochloric acid aqueous solution (1.0 L) and the organic layer was concentrated to give 138 g (yield: 94%) of the title compound as a white solid.

$^1$H NMR(500 MHz, CDCl$_3$) δ1.35-1.55 (11H, m), 1.75 (1H, m), 1.88 (1H, m), 3.08 (2H, m), 3.53(1H, m), 3.73 (2H, br d, J=5.6 Hz).

(2) Synthesis of 3-oxo-piperidine-1-carboxylic acid t-butyl ester 3-hydroxy-piperidine-1-carboxylic acid t-butyl ester (4.0 g, 20 mmol) synthesized in Section (1) was dissolved in a mixed solution (2:1:2, 100 mL) of toluene, water and ethyl ester, and 1.0 mol% TEMPO (31 mg), and NaBr (2.3 g) were sequentially added thereto. A mixture of NaHCO$_3$ (4.7 g) and NaOCl (5%, 36 mL) was slowly added to the mixture under cooling conditions (0 to 4° C.). After the reaction was complete, the organic layer was dried over anhydrous magnesium sulfate and filtered. The filtered organic layer was concentrated under reduced pressure to afford 3.8 g (yield: 95%) of the title compound.

$^1$H NMR (500 MHz, CDCl$_3$) δ1.47 (s, 9H), 1.98 (m, 2H), 2.47 (t, J=6.7 Hz, 2H), 3.59 (t, J=6.1 Hz, 2H), 4.00 (bs, 2H).

(3) Synthesis of 3-oxo-4-(2,2,2-trichloroacetyl)-piperidine-1-carboxylic acid t-butyl ester 3-oxo-piperidine-1-carboxylic acid t-butyl ester (7.7 g, 38.4 mmol) synthesized in Section (2) was dissolved in anhydrous THF (60 mL) and the resulting solution was added with stirring to 1.0 M LHMDS (46 mL) under cooling conditions (−10 to −5° C.), followed by stirring for 30 min. Ethyl trifluoroacetate (6.6 g) was added dropwise to the mixture under the same cooling conditions. The reaction was slowly warmed to room temperature and was terminated by the addition of a saturated acidic aqueous solution (100 mL). The reaction solution was extracted two times with ethyl acetate (100 mL), dried over anhydrous magnesium sulfate and filtered. The extract was distilled under reduced pressure to afford 9.5 g (yield: 80%) of the title compound.

$^1$H NMR (500 MHz, CDCl$_3$) δ1.48 (s, 9H), 2.58 (bt, 2H), 3.57 (t, J=5.8 Hz, 2H), 4.23 (bs, 2H).

(4) Synthesis of 2,4-bis-trifluoromethyl-5,8-dihydro-6H-pyrido[3,4-d]pyrimidine-7(8H)-carboxylic acid t-butyl ester 3-oxo-4-(2,2,2-trichloroacetyl)-piperidine-1-carboxylic acid t-butyl ester (2.96 g, 10 mmol) synthesized in Section (3) was dissolved in pyridine (10 mL) and was slowly added with stirring to trifluoroacetamidine (2.0 g) at 80° C. After the reaction was complete, pyridine was removed by distillation under reduced pressure. The resulting concentrate was dissolved in methylene chloride and washed with a 1.0 N hydrochloric acid aqueous solution. The organic layer was distilled under reduced pressure to afford 3.24 g of the title compound.

$^1$H NMR (500 MHz, CDCl$_3$) δ1.50 (s, 9H), 3.12 (bt, 2H), 3.78 (t, J=5.8 Hz, 2H), 4.85 (s, 2H).

(5) Synthesis of 2,4-bis-trifluoromethyl-5,6,7,8-tetrahydropyrido[3,4-d]pyrimidine hydrochloride 2,4-bis-trifluoromethyl-5,8-dihydro-6H-pyrido[3,4-d]pyrimidine-7(8H)-carboxylic acid t-butyl ester (7.5 g, 20 mmol) synthesized in Section (4) was dissolved in 100 mL of ethyl acetate which had been saturated with hydrochloric acid gas, and the mixture was stirred at room temperature for 1 hour. The solvent and the remaining hydrochloric acid gas were distilled off under reduced pressure, and the resulting brown solid was slurried using t-butylmethyl ether for 1 hour. The residue was filtered to afford 5.1 g of the title compound.

$^1$H NMR (400 MHz, CD$_3$OD) δ3.41 (t, J=6.4 Hz, 2H), 3.68 (t, J=6.4 Hz,'2H), 4.66 (s, 2H).

PREPARATION EXAMPLE 2

Synthesis of 2,4-bis-trifluoromethyl-5,6,7,8-tetrahydropyrido[3,4-d]pyrimidine hydrochloride derivatives Analogously to the procedure of Preparation Example 1, the following derivatives were synthesized.
(1) 2-propyl-4-trifluoromethyl-5,6,7,8-tetrahydropyrido[3,4-d]pyrimidine hydrochloride
(2) 2-t-butyl-4-trifluoromethyl-5,6,7,8-tetrahydro-pyrido[3,4-d]pyrimidine hydrochloride
(3) 2-cyclobutyl-4-trifluoromethyl-5,6,7,8-tetrahydro-pyrido[3,4-d]pyrimidine hydrochloride
(4) 2-pyridin-4-yl-4-trifluoromethyl-5,6,7,8-tetrahydro-pyrido[3,4-d]pyrimidine hydrochloride
(5) 2-furan-2-yl-4-trifluoromethyl-5,6,7,8-tetrahydro-pyrido[3,4-d]pyrimidine hydrochloride
(6) 2-(2-methoxy-ethyl)-4-trifluoromethyl-5,6,7,8-tetrahydro-pyrido[3,4-d]Pyrimidine hydrochloride
(7) 2-thiophen-3-yl-4-trifluoromethyl-5,6,7,8-tetrahydro-pyrido[3,4-d]pyrimidine hydrochloride
(8) 2-(4-fluoro-phenyl)-4-trifluoromethyl-5,6,7,8-tetrahydro-pyrido[3,4-d]pyrimidine hydrochloride

PREPARATION EXAMPLE 3

Synthesis of 3,3-difluoro piperidine-2,6-dione (1) Synthesis of 2,2-difluoropentanedioic acid diethyl ester Commercially available ethyl bromodifluoroacetate (16 mL, 120 mmol) and ethyl acrylate (11 mL, 100 mmol) were dissolved in tetrahydrofuran (100 mL), and copper powder (15.2 g, 240 mmol) and TMEDA (16.7 mL, 110 mmol) were sequentially added thereto at room temperature. After stirring for about 8 hours, the reaction was terminated by the addition of a saturated aqueous solution of 1.0 N hydrochloric acid and was extracted two times with toluene. The reaction solution was distilled under reduced pressure and the concentrated title compound was directly used in the subsequent step without further purification.

$^1$H NMR (500 MHz, CDCl$_3$) δ1.25 (t, J=7.2 Hz, 3H), 1.35 (t, J=7.2 Hz, 3H), 2.41 (m, 2H), 2.52 (m, 2H), 4.15 (q, J=7.2 Hz, 2H), 4.32 (q, J=7.2 Hz, 2H)

(2) Synthesis of 4-carbamoyl-4,4-difluoro butyric acid ethyl ester 2,2-difluoropentanedioic acid diethyl ester (21 g) synthesized in Section (1) was dissolved in ethanol (50 mL) and 2.0 M methanolic ammonia was slowly added thereto. The mixture was stirred at room temperature for 30 min and distilled under reduced pressure to afford 18.2 g of the title compound as viscous oil, which was used in the subsequent step without further purification.

$^1$H NMR (500 MHz, CDCl$_3$) δ1.25 (t, J=7.2 Hz, 3H), 2.43 (m, 2H), 2.54 (m, 2H), 4.14 (q, J=7.2 Hz, 2H), 5.92 (br s, 1H), 6.30 (br s, 1H)

(3) Synthesis of 3,3-difluoro piperidine-2,6-dione 4-carbamoyl-4,4-difluoro butyric acid ethyl ester (18 g) synthesized in Section (2) was dissolved in ethanol (100 mL) and a 1.0 N sodium ethoxide ethanol solution (105 mL) was slowly added thereto. After stirring for 3 hours at room temperature, the mixture was adjusted to a pH of 3 to 4 by addition of 3.0 N hydrochloric acid in dioxane, and the resulting NaCl was removed by filtration. The highly viscous oil was slurried with diethyl ether (100 mL). The resulting white solid was filtered and dried to give 11.4 g of the title compound.

$^1$H NMR (500 MHz, DMSO-d$_6$) δ2.56 (m, 2H), 2.71 (t, J=6.8 Hz, 2H), 11.60 (br s, 1H)

PREPARATION EXAMPLE 4

Synthesis of (3S)-t-butoxycarbonylamino-4-(3,3-difluoro-2-hydroxy-6-oxo-piperidin-1-yl)-butyric acid (1) Synthesis of (3S)-t-butoxycarbonylamino-4-hydroxy butyric acid i-propyl ester Commercially available (2S)-t-butoxycarbonylamino-succinic acid 4-i-propyl ester (2.8 g, 10.3 mmol) was dissolved in tetrahydrofuran (10 mL) and N-methylmorpholine (1.13 mL) was added thereto. The mixture was cooled to −10° C. i-butyl chloroformate (1.40 mL) was added to the mixture which was then stirred for 10 min to form an active ester. After removing the resulting ammonium hydrochloric acid salt by filtration, NaBH$_4$ (0.59 g) in water was added dropwise to the filtrate and the reaction was terminated by the addition of saturated NH$_4$Cl. The resulting reaction slurry was extracted two times with ethyl acetate and the organic layer was dried over anhydrous magnesium sulfate and filtered. The filtrate was distilled under reduced pressure to afford 2.51 g (yield: 95%) of the title compound as a pale yellow oil.

$^1$H NMR (400 MHz, CDCl$_3$) δ1.22 (d, J=6.8, 6H), 1.44 (s, 9H), 2.54-2.62 (m, 2H), 3.65 (d, J=4.0, 2H), 3.99 (bs 1H), 5.02 (m, 1H), 5.36 (bs, 1H).

(2) Synthesis of (3S)-t-butoxycarbonylamino-4-(3,3-difluoro-2,6-dioxo-piperidin-1-yl)-butyric acid i-propyl ester (3S)-t-butoxycarbonylamino-4-hydroxy butyric acid i-propyl ester (5.3 g, 20 mmol) synthesized in Section (1) and 3,3-difluoro piperidine-2,6-dione (3.6 g, 26 mmol) synthesized in Preparation Example 3 were dissolved in methylene chloride (20 mL), and cooled to a temperature of 0 to 5° C. Triphenylphosphine (6.3 g) and 2.2 M DEAD (11 mL) in toluene were sequentially added, and a reaction temperature was slowly warmed to ambient temperature. After stirring for 4 hours, the reaction was directly subjected to column chromatography without a particular termination step, thus affording 5.5 g (yield: 70%) of the title compound.

$^1$H NMR (400 MHz, CDCl$_3$) δ1.22 (m, 6H), 1.35 (s, 9H), 2.33-2.56 (m, 4H), 2.87 (m, 2H), 3.70 (br d, J=11.8, 1H), 4.07-4.19 (m, 31-1), 5.04 (m, 1H), 5.11 (br d, J=9.8, 1H).

(3) Synthesis of (3S)-t-butoxycarbonyl-4-(3,3-difluoro-2-hydroxy-6-oxo-piperidin-1-yl)-butyric acid i-propyl ester (3S)-t-butoxycarbonylamino-4-(3,3-difluoro-2,6-dioxo-piperidin-1-yl)-butyric acid i-propyl ester (5.5 g, 14 mmol) synthesized in Section (2) was dissolved in a mixed solvent of tetrahydrofuran and methanol (2:1, 60 mL) and cooled to a temperature of 0 to 5° C. 1.0 equivalent of NaBH$_4$ (530 mg) were added and the mixture was stirred for 30 min while maintaining the cooling temperature. The reaction was terminated by the addition of a saturated NH$_4$Cl aqueous solution and purified by column chromatography to give 4.0 g of the title compound.

$^1$H NMR (500 MHz, CDCl$_3$) δ1.22 (m, 6H), 1.41 (br s, 9H), 2.15 (m, 1H), 2.45-2.70 (m, 5H), 3.05 (m, 0.4H), 3:42 (m, 0.6H), 3.80 (m, 0.6H), 4.10-4.35 (m, 2.4H), 4.88-5.10 (m, 2H), 5.35-5.60 (m, 1.6H), 6.15 (br s, 0.4H)

(4) Synthesis of (3S)-t-butoxycarbonylamino-4-(3,3-difluoro-2-hydroxy-6-oxo-piperidin-1-yl)-butyric acid (3 S)-t-butoxycarbonyl-4-(3,3-difluoro-2-hydroxy-6-oxo-piperidin-1-yl)-butyric acid i-propyl ester (4.0 g, 10 mmol) synthesized in Section (3) was dissolved in a mixed solvent of tetrahydrofuran, $H_2O$ and methanol (1:1:1, 30 mL) and lithium hydroxide hydrate (630 mg) was added thereto at room temperature. After 2 hours, the reaction solution was diluted with 100 mL of distilled water, and impurities were washed with methylene chloride (50 mL). The basic aqueous solution was adjusted to a pH of 3.0 to 4.0 by addition of a strong acidic aqueous solution and the resulting white slurry was extracted two times with methylene chloride. The organic extract was distilled under reduced pressure to provide 1.9 g of the concentrated title compound, which was used in the subsequent step without further purification.

$^1$H NMR (500 MHz, DMSO-$d_6$) δ1.31 (br s, 9H), 2.05 (m, 1H), 2.20-2.50 (m, 5H), 2.85 (m, 0.6H), 3.05 (m, 0.4H), 3.60 (m, 2H), 3.98 (m, 1), 4.80 (m, 1H), 6.50 (br s, 0.4H), 6.75 (br s, 0.6H), 7.02 (m, 1H), 12.05 (br s, 1H)

PREPARATION EXAMPLE 5

Synthesis of [3(S)-(2,4-bis-trifluoromethyl-5,8-dihydro-6H-pyrido[3,4-d]pyrimidin-7-yl)-1-(3,3-difluoro-2-hydroxy-6-oxo-pyridin-1-ylmethyl)-3-oxo-propyl]carbamic acid t-butyl ester (3S)-t-butoxycarbonylamino-4-(3,3-difluoro-2-hydroxy-6-oxo-piperidin-1-yl)-butyric acid (2.6 g, 4 mmol) synthesized in Preparation Example 4 and 2,4-bis-trifluoromethyl-5,6,7,8-tetrahydropyrido[3,4-d]pyrimidine hydrochloride (1.4 g) synthesized in Preparation Example 1 were dissolved in methylene chloride (50 mL) and cooled to a temperature of 0 to 4° C. HOBT (650 mg), diisopropylethylamine (2.2 mL) and EDCI (1.20 g) were sequentially added thereto, and a reaction temperature was slowly elevated to room temperature. After stirring for 6 hours, the reaction solution was washed with a 1.0 N hydrochloric acid aqueous solution, and the organic layer was distilled under reduced pressure to afford 2.6 g of the title compound.

$^1$H NMR (500 MHz, CDCl$_3$) δ1.31 (m, 9H), 2.14 (m, 1H), 2.30-2.85 (m, 3H), 2.90-3.30 (m, 3H), 3.45 (m, 0.5H), 3.60-4.30 (m, 3H), 4.75-5.05 (m, 2H), 5.95-6.50 (m, 1H)

PREPARATION EXAMPLE 6

Synthesis of [(S)-1-(3,3-difluoro-2-hydroxy-6-oxo-piperidin-1-ylmethyl)-3-oxo-(2-propyl-4-trifluoromethyl-5,8-dihydro-6H-pyrido[3,4-d]pyrimidin-7-yl)-propyl]-carbamic acid t-butyl ester (3S)-t-butoxycarbonylamino-4-(3,3-difluoro-2-hydroxy-6-oxo-piperidin-1-yl)-butyric acid (20 mg, 0.06 mmol) synthesized in Preparation Example 4 and 2-propyl-4-trifluoromethyl-5,6,7,8-tetrahydropyrido[3,4-d]pyrimidine hydrochloride (22 mg) synthesized in Preparation Example 2-(1) were dissolved in dimethylformaldehyde (2 mL) and cooled to a temperature of 0 to 4° C. HOBT (650 mg), diisopropylethylamine (2.2 mL) and EDCI (1.20 g) were sequentially added thereto and a reaction temperature was slowly elevated to room temperature. After the reaction solution was stirred for 10 hours, an ammonium chloride aqueous solution was added and the organic layer was extracted with ethyl acetate. The residue was purified by prep-TLC to give 7.4 mg (yield: 22%) of the title compound.

$^1$H NMR (400 MHz, CDCl$_3$) δ0.98-1.02 (m, 3H), 1.26-1.30 (m, 2H), 1.40-1.46 (m, 9H), 1.75-1.86 (m, 3H), 2.17 (m, 1H), 2.55-2.69 (m, 3H), 2.88-3.10 (m, 5H), 3.49-4.31 (m, 4H), 4.70-4.96 (m, 3H) MS(m/e) 602 (M+Na)

EXAMPLE 1

Synthesis of 1-[(2S)-amino-4-(2,4-bis-trifluoromethyl-5,8-dihydro-6H-pyrido[3,4-d]pyrimidin-7-yl)-4-oxo-butyl]-5,5-difluoro-(6R)-hydroxy-piperidin-2-one hydrochloride

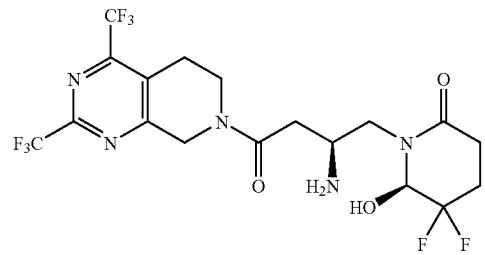 [SMILES: N[C@@H](CC(=O)N1CCc2c(nc(C(F)(F)F)nc2C(F)(F)F)C1)CN1C(=O)CCC(F)(F)[C@H]1O]

[3(S)-(2,4-bis-trifluoromethyl-5,8-dihydro-6H-pyrido[3,4-d]pyrimidin-7-yl)-1-(3,3-difluoro-2-hydroxy-6-oxo-pyridin-1-ylmethyl)-3-oxo-propyl]-carbamic acid t-butyl ester (2.0 g) synthesized in Preparation Example 5 was a diastereomeric mixture which was then into two isomers by silica gel column chromatography. Out of the separated isomers, the isomer having a relatively high polarity was dissolved in ethyl acetate (10 mL), treated with commercially available 4.0 N hydrogen chloride in dioxane and was stirred for 30 min. The reaction solution was distilled under reduced pressure and the viscous oil was slurried with t-butylmethyl ether (10 mL). The resulting slurry was filtered and dried to afford 500 mg of the title compound.

$^1$H NMR (500 MHz, DMSO-d$_6$) δ2.16 (m, 1H), 2.35-2.55 (m, 2H), 2.78-2.88 (m, 2H), 2.95-3.18 (m, 2H), 3.40 (m, 1H), 3.70 (m, 1H), 3.82 (m, 2H), 4.90 (m, 2H), 7.30 (br s, 1H), 7.95 (m, 3H)

EXAMPLE 2

Synthesis of 1-[(2S)-amino-4-(2,4-bis-trifluoromethyl-5,8-dihydro-6H-pyrido[3,4-d]pyrimidin-7-yl)-4-oxo-butyl]-5,5-difluoro-(6S)-hydroxy-piperidin-2-one hydrochloride

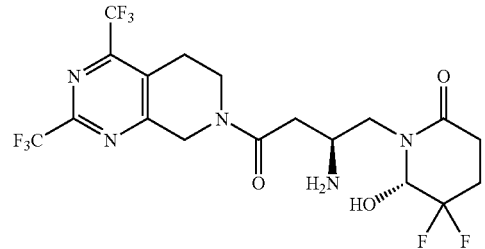 [SMILES: N[C@@H](CC(=O)N1CCc2c(nc(C(F)(F)F)nc2C(F)(F)F)C1)CN1C(=O)CCC(F)(F)[C@@H]1O]

Analogously to Example 1, the diastereomeric mixture synthesized in Preparation Example 5 was subjected to column chromatography to separate a relatively low polarity isomer which was then dissolved in ethyl acetate (10 mL), followed by the treatment with a solution of commercially available 4.0 N hydrogen chloride in dioxane and stirring for 30 min. The reaction solution was distilled under reduced pressure, and the resulting concentrate was slurried with t-butylmethyl ether (10 mL). The resulting slurry was filtered and dried to afford 250 mg of the title compound.

$^1$H NMR (500 MHz, DMSO-$d_6$) δ2.13 (m, 1H), 2.35-2.55 (m, 2H), 2.75-2.90 (m, 2H), 2.98 (br s, 1H), 3.12 (br s, 1H), 3.50-3.74 (m, 2H), 3.80 (m, 3H), 3.82 (m, 2H), 4.90 (m, 2H), 7.25 (br s, 1H), 7.95 (m, 3H).

EXAMPLE 3

Synthesis of 1-[(S)-2-amino-4-oxo-4-(2-propyl-4-trifluoromethyl-5,8-dihydro-6H-pyrido[3,4-d]pyrimidin-7-yl)-butyl]-5,5-difluoro-6-hydroxy-piperidin-2-one hydrochloride

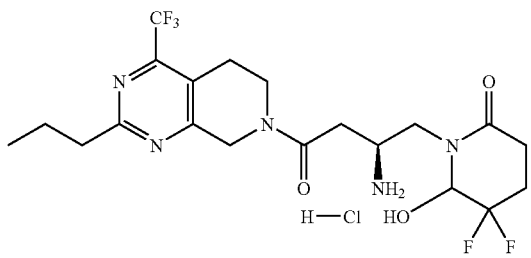

The compound synthesized in Preparation Example 6 was treated with a solution of commercially available 4.0 N hydrogen chloride in dioxane and was stirred for 1 hour. The reaction solution was distilled under reduced pressure and purified by prep-TLC to afford 4.7 mg (yield: 77%) of the title compound.

$^1$H NMR (400 MHz, MeOH-$d_4$) δ0.87-0.91 (m, 3H), 1.72-1.80 (m, 3H), 2.45-2,64 (m, 6H), 2.81-3.06 (m, 4H), 3.25-3.80 (m, 5H), 4.19-4.78 (m, 3H); MS (m/e) 480 (M+1)

PREPARATION EXAMPLE 7

Synthesis of [(S)-3-(2-t-butyl-4-trifluoromethyl-5,8-dihydro-6H-pyrido[3,4-d]pyrimidin-7-yl)-1-(3,3-difluoro-2-hydroxy-6-oxo-piperidin-1-ylmethyl)-3-oxo-propyl]-carbamic acid t-butyl ester Analogously to the procedure of Preparation Example 6, (3S)-t-butoxycarbonylamino-4-(3,3-difluoro-2-hydroxy-6-oxo-piperidin-1-yl)-butyric acid (26 mg, 0.07 mmol) synthesized in Preparation Example 4 and 2-t-butyl-4-trifluoromethyl-5,6,7,8-tetrahydro-pyrido[3,4-d]pyrimidine hydrochloride (30 mg) synthesized in Preparation Example 2-(2) were coupled to afford 15.5 mg (yield: 36%) of the title compound.

$^1$H NMR (400 MHz, MeOH-$d_4$) δ1.38-1.42 (m, 18H), 2.16-2.24 (m, 2H), 2.58-2.72 (m, 5H), 2.99-3.12 (m, 3H), 3.81-3.89 (m, 3H), 4.30 (m, 1H), 4.74-4.97 (m, 3H); MS (m/e) 616 (M+Na)

EXAMPLE 4

Synthesis of 1-[(S)-2-amino-4-(2-t-butyl-4-trifluoromethyl-5,8-dihydro-6H-pyrido[3,4-d]pyrimidin-7-yl)-4-oxo-butyl]-5,5-difluoro-6-hydroxy-piperidin-2-one hydrochloride

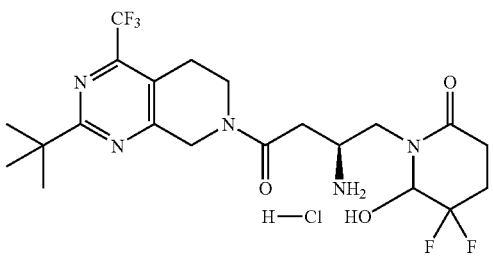

Analogously to the procedure of Example 3, 10.5 mg (yield: 76%) of the title compound was obtained using the compound synthesized in Preparation Example 7.

$^1$H NMR (400 MHz, MeOH-$d_4$) δ1.30 (d, 91-1), 2.07 (b, 1H), 2.42-2.56 (m, 4H), 2.61-2.98 (m, 3H), 3.21-3.30 (m, 2H), 3.70-3.80 (m, 3H), 4.69-4.79 (m, 3H); MS (m/e) 494 (M+1)

PREPARATION EXAMPLE 8

Synthesis of [(S)-3-(2-cyclo-4-trifluoromethyl-5,8-dihydro-6H-pyrido[3,4-d]pyrimidin-7-yl)-1-(3,3-difluoro-2-hydroxy-6-oxo-piperidin-1-ylmethyl)-3-oxo-propyl]-carbamic acid t-butyl ester Analogously to the procedure of Preparation Example 6, (3S)-t-butoxycarbonylamino-4-(3,3-difluoro-2-hydroxy-6-oxo-piperidin-1-yl)-butyric acid (26 mg, 0.07 mmol) synthesized in Preparation Example 4 and 2-cyclobutyl-4-trifluoromethyl-5,6,7,8-tetrahydro-pyrido[3,4-d]pyrimidine hydrochloride (30 mg) synthesized in Preparation Example 2-(3) were coupled to afford 14.6 mg (yield: 34%) of the title compound.

$^1$H NMR (400 MHz, MeOH-$d_4$) δ1.39 (m, 9H), 1.96-2.24 (m, 41-1), 2.38-2.74 (m, 9H), 2.99-3.12 (m, 3H), 3.82-3.89 (m, 4H), 4.30 (m, 1H), 4.78-4.97 (m, 3H); MS (m/e) 614 (M+Na)

EXAMPLE 5

Synthesis of 1-[(S)-2-amino-4-(2-cyclobutyl-4-trifluoromethyl-5,8-dihydro-6H-pyrido[3,4-d]pyrimidin-7-yl)-4-oxo-butyl]-5,5-difluoro-6-hydroxy-piperidin-2-one hydrochloride

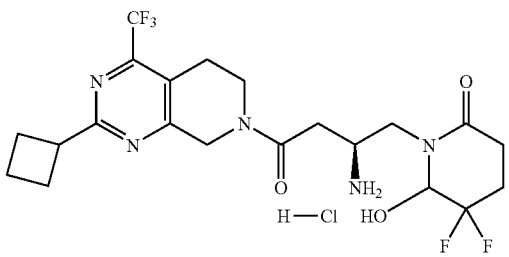

Analogously to the procedure of Example 3, 13 mg of the title compound was quantitatively obtained using the compound of Preparation Example 8.

$^1$H NMR (400 MHz, MeOH-$d_4$) δ1.87-2.02 (m, 3H), 2.26-2.52 (m, 9H), 2.89-2.99 (m, 2H), 3.21-3.25 (m, 2H), 3.70-3.80 (m, 4H), 3.99-4.80 (m, 3H); MS (m/e) 492 (M+1)

PREPARATION EXAMPLE 9

Synthesis of [(S)-1-(3,3-difluoro-2-hydroxy-6-oxo-piperidin-1-ylmethyl)-3-oxo-3-(2-pyridin-4-yl-4-trifluoromethyl-5,8-dihydro-6H-pyrido[3,4d]pyrimidin-7-yl)-propyl]-carbamic acid t-butyl ester Analogously to the procedure of Preparation Example 6, (3S)-t-butoxycarbonylamino-4-(3,3-difluoro-2-hydroxy-6-oxo-piperidin-1-yl)-butyric acid (24 mg, 0.07 mmol) synthesized in Preparation Example 4 and 2-pyridin-4-yl-4-trifluoromethyl-5,6,7,8-tetrahydro-pyrido[3,4-d]pyrimidine hydrochloride (30 mg) synthesized in Preparation Example 2-(4) were coupled to afford 13.5 mg (yield: 32%) of the title compound.

$^1$H NMR (400 MHz, MeOH-d$_4$) δ1.37 (m, 9H), 2.16-2.26 (m, 2H), 2.59-2.88 (m, 5H), 3.01-3.22(m, 3H), 3.37-3.94 (m, 3H), 4.30 (m, 1H), 4.92-5.01 (m, 3H), 8.28 (m, 2H), 8.75 (m, 1H); MS (m/e) 637 (M+Na)

EXAMPLE 6

Synthesis of 1-[(S)-2-amino-4-oxo-4-(2-pyridin-4-yl-4-trifluoromethyl-5,8-dihydro-6H-pyrido[3,4-d]pyrimidin-7-yl)-butyl]-5,5-difluoro-6-hydroxy-piperidin-2-one

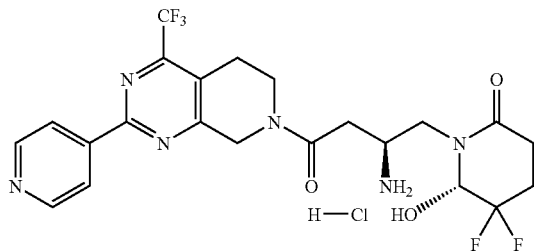

The compound synthesized in Preparation Example 9 was treated with commercially available 4.0 N hydrogen chloride in dioxane and was stirred for 1 hour. Since the title compound was a diastereomeric compound, the reaction solution was distilled under reduced pressure and separated into two isomers by prep-TLC. Out of the separated isomers, 2 mg of the title compound with a relatively low polarity was obtained.

$^1$H NMR (400 MHz, MeOH-d$_4$) δ2.17 (m, 1H), 2.58-2.68 (m, 4H), 2.77-2.82 (m, 1H), 3.11-3.21 (m, 2H), 3.34-3.70(m, 2H), 3.91-4.00 (m, 3H), 4.77-5.06 (m, 3H), 8.44 (d, 2H, J=6.0 MHz), 8.76 (d, 2H, J=4.8 MHz); MS (m/e) 515 (M+1)

EXAMPLE 7

Synthesis of 1-[(S)-2-amino-4-oxo-4-(2-pyridin-4-yl-4-trifluoromethyl-5,8-dihydro-6H-pyrido[3,4-d]pyrimidin-7-yl)-butyl]-5,5-difluoro-6-hydroxy-piperidin-2-one hydrochloride

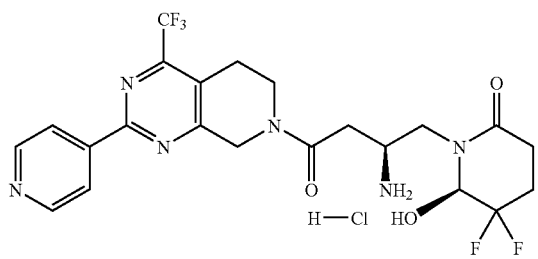

The compound synthesized in Preparation Example 9 was treated with commercially available 4.0 N hydrogen chloride in dioxane and was stirred for 1 hour. Since the title compound was a diastereomeric compound, the reaction solution was distilled under reduced pressure and separated into two isomers by prep-TLC. Out of the separated isomers, 1.8 mg of the title compound with a relatively high polarity was obtained.

$^1$H NMR (400 MHz, MeOH-d$_4$) δ2.17 (m, 1H), 2.53-2.65 (m, 4H), 2.74-2.80 (m, 1H), 3.06-3.20 (m, 2H), 3.34-3.66 (m, 2H), 3.82-4.00 (m, 3H), 4.77-5.00 (m, 3H), 8.43 (d, 2H, J=6.0 MHz), 8.76 (d, 2H, J=4.4 MHz); MS (m/e) 515 (M+1)

PREPARATION EXAMPLE 10

Synthesis of [(S)-1-(3,3-difluoro-2-hydroxy-6-oxo-piperidin-1-ylmethyl)-3-(2-furan-2-yl-4-trifluoromethyl-5,8-dihydro-6H-pyrido[3,4-d]pyrimidin-7-yl)-3-oxo-propyl]-carbamic acid t-butyl ester Analogously to the procedure of Preparation Example 6, (3S)-t-butoxycarbonylamino-4-(3,3-difluoro-2-hydroxy-6-oxo-piperidin-1-yl)-butyric acid (25 mg, 0.07 mmol) synthesized in Preparation Example 4 and 2-furan-2-yl-4-trifluoromethyl-5,6,7,8-tetrahydro-pyrido[3,4-d]pyrimidine hydrochloride (30 mg) synthesized in Preparation Example 2-(5) were coupled to afford 18.1 mg (yield: 43%) of the title compound.

$^1$H NMR (400 MHz, MeOH-d$_4$) δ1.28 (m, 9H), 2.13 (m, 1H), 2.39-2.47 (m, 3H), 2.61-2.76 (m, 2H), 2.89-3.03 (m, 3H), 3.56-3.80 (m, 3H), 4.31 (m, 1H), 4.70-4.86 (m, 3H), 6.55-6.56 (m, 1H), 7.28 (d, 1H, J=4.0 MHz), 7.52-7.57 (m, 1H); MS (m/e) 626 (M+Na)

EXAMPLE 8

Synthesis of 1-[(S)-2-amino-4-(2-furan-2-yl-4-trifluoromethyl-5,8-dihydro-6H-pyrido[3,4-d]pyrimidin-7-yl)-butyl]-4-oxo-butyl]-5,5-difluoro-6-hydroxy-piperidin-2-one hydrochloride

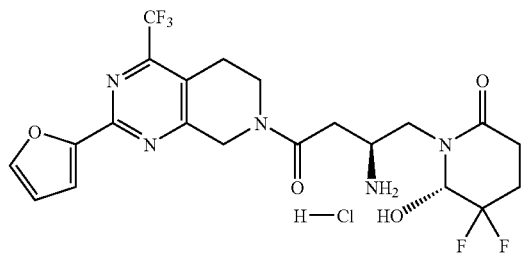

Analogously to the procedure of Example 6, two isomers were separated from the compound synthesized in Preparation Example 10. Out of the separated isomers, 4.7 mg of the title compound having a relatively low polarity was obtained.

$^1$H NMR (400 MHz, MeOH-d$_4$) δ2.17 (m, 1H), 2.45-2.81 (m, 5H), 3.04-3.17 (m, 2H), 3.33-3.72 (m, 2H), 3.87-3.96 (m, 3H), 4.90-5.00 (m, 3H), 6.68 (s, 1H), 7.41 (d, 1H, J=3.2 MHz), 7.79 (s, 1H); MS (m/e) 504 (M+1)

EXAMPLE 9

Synthesis of 1-[(S)-2-amino-4-(2-furan-2-yl-4-trifluoromethyl-5,8-dihydro-6H-pyrido[3,4-d]pyrimidin-7-yl)-butyl]-4-oxo-butyl]-5,5-difluoro-6-hydroxy-piperidin-2-one hydrochloride

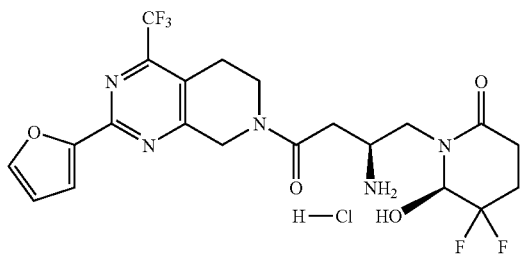

Analogously to the procedure of Example 6, two isomers were separated from the compound synthesized in Preparation Example 10. Out of the separated isomers, 4.8 mg of the title compound having a relatively high polarity was obtained.
$^1$H NMR (400 MHz, MeOH-$d_4$) δ2.17 (m, 1H), 2.51-2.76 (m, 5H), 3.03-3.11 (m, 2H), 3.34-3.70 (m, 2H), 3.84-3.93 (m, 3H), 4.82-4.90 (m, 3H), 6.68 (s, 1H), 7.41 (d, 1H, J=3.6 MHz), 7.79 (s, 1H); MS (m/e) 504 (M+1)

PREPARATION EXAMPLE 11

Synthesis of {(S)-1-(3,3-difluoro-2-hydroxy-6-oxo-piperidin-1-ylmethyl)-3-[2-(2-methoxy-ethyl-4-trifluoromethyl-5,8-dihydro-6H-pyrido[3,4-d]pyrimidin-7-yl]-3-oxo-propyl}-carbamic acid t-butyl ester Analogously to the procedure of Preparation Example 6, (3S)-t-butoxycarbonylamino-4-(3,3-difluoro-2-hydroxy-6-oxo-piperidin-1-yl)-butyric acid (61 mg, 0.17 mmol) synthesized in Preparation Example 4 and 2-(2-methoxy-ethyl)-4-trifluoromethyl-5,6,7,8-tetrahydro-pyrido[3,4-d]pyrimidine hydrochloride (65 mg) synthesized in Preparation Example 2-(6) were coupled to afford 38.2 mg (yield: 37%) of the title compound.
$^1$H NMR (400 MHz, MeOH-$d_4$) δ1.31-1.44 (m, 9H), 2.17-2.24 (m, 2H), 2.58-3.74 (m, 4H), 2.88-3.37 (m, 10H), 3.85-3.98 (m, 41-1), 4.29 (m, 1H), 4.75-4.96 (m, 3H); MS (m/e) 618 (M+Na)

EXAMPLE 10

Synthesis of 1-{(S)-2-amino-4-[2-(2-methoxy-ethyl)-4-trifluoromethyl-5,8-dihydro-6H-pyrido[3,4-d]pyrimidin-7-yl]-4-oxo-butyl}-5,5-difluoro-6-hydroxy-piperidin-2-one hydrochloride

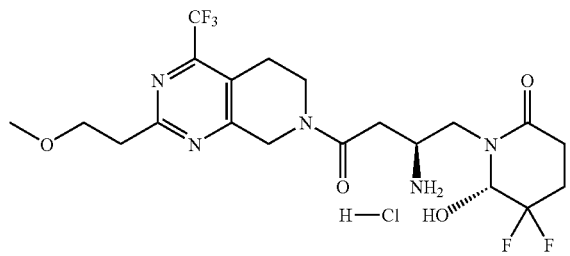

Analogously to the procedure of Example 6, two isomers were separated from the compound synthesized in Preparation Example 11. Out of the separated isomers, 6.2 mg of the title compound having a relatively low polarity was obtained.
$^1$H NMR (400 MHz, MeOH-$d_4$) δ2.18 (m, 1H), 2.62-2.78 (m, 4H), 3.02-3.42 (m, 10H), 3.68-4.06 (m, 5H), 4.80-4.90 (m, 3H); MS (m/e) 496 (M+1)

EXAMPLE 11

Synthesis of 1-{(S)-2-amino-4-[2-(2-methoxy-ethyl)-4-trifluoromethyl-5,8-dihydro-6H-pyrido[3,4-d]pyrimidin-7-yl]-4-oxo-butyl}-5,5-difluoro-6-hydroxy-piperidin-2-one hydrochloride

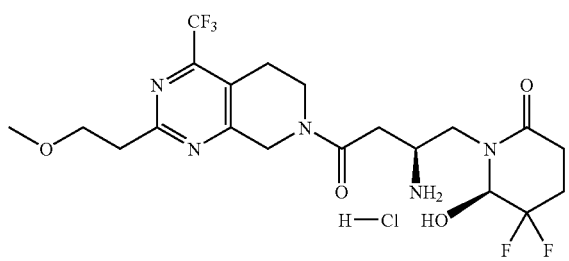

Analogously to the procedure of Example 6, two isomers were separated from the compound synthesized in Preparation Example 11. Out of the separated isomers, 9.1 mg of the title compound having a relatively high polarity was obtained.
$^1$H NMR (400 MHz, MeOH-$d_4$) δ2.21 (m, 1H), 2.60-2.64 (m, 3H), 2.87-3.37 (m, 11H), 3.61-4.02 (m, 5H), 4.79-4.99 (m, 3H); MS (m/e) 496 (M+1)

PREPARATION EXAMPLE 12

Synthesis of {(S)-1-(3,3-difluoro-2-hydroxy-6-oxo-piperidin-1-ylmethyl)-3-oxo-3-(2-thiophen)-3-yl-4-trifluoromethyl-5,8-dihydro-6H-pyrido[3,4-d]pyrimidin-7-yl)-propyl]-carbamic acid t-butyl ester Analogously to the procedure of Preparation Example 6, (3S)-t-butoxycarbonylamino-4-(3,3-difluoro-2-hydroxy-6-oxo-piperidin-1-yl)-butyric acid (39 mg, 0.11 mmol) synthesized in Preparation Example 4 and 2-thiophen-3-yl-4-trifluoromethyl-5,6,7,8-tetrahydro-pyrido[3,4-d]pyrimidine hydrochloride (50 mg) synthesized in Preparation Example 2-(7) were coupled to afford 26 mg (yield: 38%) of the title compound.
$^1$H NMR (400 MHz, MeOH-$d_4$) δ1.40 (s, 9H), 2.16-2.25 (m, 2H), 2.59-2.75 (m, 5H), 3.01-3.13 (m, 3H), 3.83-3.93 (m, 3H), 4.31 (m, 1H), 4.88-4.98 (m, 3H), 7.51-7.53 (m, 1H), 7.89 (d, 1H, J=4.4 MHz), 8.40 (s, 1H); MS (m/e) 642 (M+Na)

EXAMPLE 12

Synthesis of 1-[(S)-2-amino-4-oxo-4-(2-thiophen-3-yl-4-trifluoromethyl-5,8-dihydro-6H-pyrido[3,4-d]pyrimidin-7-yl)-butyl]-5,5-difluoro-6-hydroxy-piperidin-2-one hydrochloride

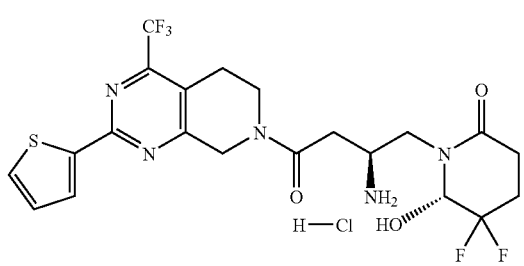

Analogously to the procedure of Example 6, two isomers were separated from the compound synthesized in Preparation Example 12. Out of the separated isomers, 6.2 mg of the title compound having a relatively low polarity was obtained.

$^1$H NMR (400 MHz, MeOH-d$_4$) δ2.18 (m, 1H), 2.58-2.67 (m, 4H), 2.77-2.81 (m, 1H), 3.04-3.12 (m, 2H), 3.34-3.42 (m, 2H), 3.81-3.96 (m, 3H), 4.90-4.97 (m, 3H), 7.52-7.55 (m, 1H), 7.89 (d, 1H, J=5.2 MHz), 8.40-8.41 (m, 1H); MS (m/e) 520 (M+1)

EXAMPLE 13

Synthesis of 1-[(S)-2-amino-4-oxo-4-(2-thiophen-3-yl-4-trifluoromethyl-5,8-dihydro-6H-pyrido[3,4-d]pyrimidin-7-yl)-butyl]-5,5-difluoro-6-hydroxy-piperidin-2-one hydrochloride

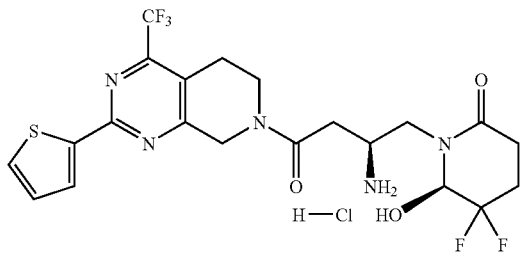

Analogously to the procedure of Example 6, two isomers were separated from the compound synthesized in Preparation Example 12. Out of the separated isomers, 5.8 mg of the title compound having a relatively high polarity was obtained.

$^1$H NMR (400 MHz, MeOH-d$_4$) δ2.17 (m, 1H), 2.55-2.65 (m, 4H), 2.80-2.85 (m, 1H), 3.04-3.12 (m, 2H), 3.46-3.51 (m, 1H), 3.66-3.74 (m, 1H), 3.86-3.95 (m, 3H), 4.85-4.93 (m, 3H), 7.52-7.55 (m, 1H), 7.89 (d, 1H, J=5.2 MHz), 8.40-8.41 (m, 1H); MS (m/e) 520 (M+1)

PREPARATION EXAMPLE 13

Synthesis of {(S)-1-(3,3-difluoro-2-hydroxy-6-oxo-piperidin-1-ylmethyl)-3-[2-(4-fluoro-phenyl)-4-trifluoromethyl-5,8-dihydro-6H-pyrido[3,4-d]pyrimidin-7-yl]-3-oxo-propyl}-carbamic acid t-butyl ester Analogously to the procedure of Preparation Example 5, (3S)-t-butoxycarbonylamino-4-(3,3-difluoro-2-hydroxy-6-oxo-piperidin-1-yl)-butyric acid (30 mg, 0.09 mmol) synthesized in Preparation Example 4 and 2-(4-fluoro-phenyl)-4-trifluoromethyl-5,6,7,8-tetrahydro-pyrido[3,4-d]pyrimidine hydrochloride (25 mg) synthesized in Preparation Example 2-(8) were coupled to afford 10.5 mg (yield: 20%) of the title compound.

$^1$H NMR (500 MHz, CDCl$_3$) δ1.41-1.44 (m, 9H), 2.57-2.61 (m, 6H), 3.12-3.14 (m, 3H), 3.91-4.00 (m, 4H), 4.86-4.96 (m, 4H), 7.16-7.18 (m, 2H), 8.46-8.49 (m, 2H); MS (m/e) 654 (M+Na)

EXAMPLE 14

Synthesis of 1-{(S)-2-amino-4-[2-(4-fluoro-phenyl)-4-trifluoromethyl-5,8-dihydro-6H-pyrido[3,4-d]pyrimidin-7-yl]-4-oxo-butyl}-5,5-difluoro-6-hydroxy-piperidin-2-one hydrochloride

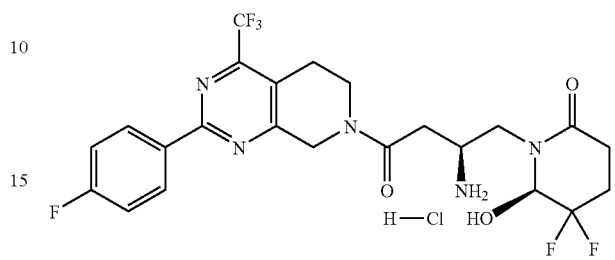

Analogously to the procedure of Example 3, 8.8 mg (yield: 93%) of the title compound was obtained using the compound synthesized in Preparation Example 13.

$^1$H NMR (500 MHz, MeOH-d$_4$) 2.55-2.64 (m, 6H), 3.00-3.38 (m, 5H), 3.86-3.93 (m, 2H), 4.84-4.92 (m, 3H), 7.21-7.24 (m, 2H), 8.48-8.51 (m, 2H); MS (m/e) 532(M+1)

PREPARATION EXAMPLE 14

Synthesis of (S)-3-t-butoxycarbonylamino-4-(3,3-difluoro-2,6-dioxo-piperidin-1-yl)-butyric acid (1) Synthesis of (S)-3-t-butoxycarbonylamino-4-hydroxy-butyric acid benzyl ester (S)-2-t-butoxycarbonylamino-succinic acid 4-benzyl ester (545 mg, 1.69 mmol) was dissolved in tetrahydrofuran (THF) to which N-methylmorpholine (NMM, 0.19 mL, 1.77 mmol) and isobutyl chloroformate (0.23 mL, 1.77 mmol) were added at 0° C., followed by stirring at that temperature for 30 min. After 30 min, the resulting white solid salt was removed by celite filtration, and a solution of sodium borohydride (96 mg, 2.53 mmol) in distilled water (2 mL) was added to the resulting clear filtrate without further concentration at room temperature. After stirring for 1 hour at room temperature, THF was distilled under reduced pressure. The reaction was diluted with ethyl acetate and was terminated by the addition of 1N HCl. The organic layer was extracted with ethyl acetate and was purified by column chromatography (ethyl acetate: hexane=1:1) to afford 468 mg (yield: 90%) of the title compound.

$^1$H NMR (500 MHz, CDCl$_3$) δ1.42 (s, 9H), 2.67 (d, 2H, J=5.5Hz), 3.67-3.68 (m, 2H), 3.99-4.01 (m, 1H), 5.12 (s, 2H), 5.29 (b, 1H), 7.33-7.36 (m, 5H); MS (m/e) 332 (M+Na)

(2) Synthesis of (S)-3-t-butoxycarbonylamino-4-(3,3-difluoro-2,6-dioxo-piperidin-1-yl)-butyric acid benzyl ester Analogously to the procedure of Preparation Example 4-(2), 1.86 g (yield: 86%) of the title compound was obtained using (S)-3-t-butoxycarbonylamino-4-hydroxy-butyric acid benzyl ester (1.5 g, 4.9 mmol) synthesized in Section (1) and 3,3-difluoro piperidine-2,6-dione (880 mg, 5.9 mmol) synthesized in Preparation Example 3.

$^1$H NMR (500 MHz, CDCl$_3$) δ1.37 (s, 9H), 2.43 (m, 2H), 2.62-2.67 (m, 2H), 2.88-2.89 (m, 2H), 3.71 (d, 1H, J=11 Hz), 4.2 (m, 2H), 5.17 (s, 2H), 5.19 (d, 1H), 7.36-7.37 (m, 5H)

(3) Synthesis of (S)-3-t-butoxycarbonylamino-4-(3,3-difluoro-2,6-dioxo-piperidin-1-yl)-butyric acid (S)-3-t-butoxycarbonylamino-4-(3,3-difluoro-2,6-dioxo-piperidin-1-yl)-butyric acid benzyl ester (310 mg, 0.70 mmol) synthesized in Section (2) was dissolved in methanol and 10% Pd/C (31 mg, 0.1 eq) was added thereto. The mixture was stirred for 1 hour under 1 atm hydrogen gas. After the reaction was complete, a solid material was removed by celite filtration to afford 260 mg of the crude title compound.

PREPARATION EXAMPLE 15

Synthesis of [(S)-3-(2,4-bis-trifluoromethyl-5,8-dihydro-6H-pyrido[3,4-d]pyrimidin-7-yl)-1-(3,3-difluoro-2,6-dioxo-piperidin-1-ylmethyl)-3-oxo-propyl]-carbamic acid t-butyl ester Analogously to the procedure of Preparation Example 5, 6.6 mg (yield: 13%) of the title compound was obtained using (S)-3-t-butoxycarbonylamino-4-(3,3-difluoro-2,6-dioxo-piperidin-1-yl)-butyric acid (30 mg, 0.09 mmol) synthesized in Preparation Example 14 and 2,4-bis-trifluoromethyl-5,6,7,8-tetrahydropyrido[3,4-d]pyrimidine hydrochloride (23 mg, 0.009 mmol) synthesized in Preparation Example 1.
$^1$H NMR (500 MHz, CDCl$_3$) δ1.37 (s, 9H), 2.42 (m, 2H), 2.76-2.95 (m, 4H), 3.14-3.28 (m, 2H), 3.71-4.22 (m, 5H), 4.85-5.00 (m, 2H), 5.52-5.55 (m, 1H); MS (m/e) 626 (M+1)

EXAMPLE 15

Synthesis of 1-[(S)-2-amino-4-(2,4-bis-trifluoromethyl-5,8-dihydro-6H-pyrido[3,4-d]pyrimidin-7-yl)-4-oxo-butyl]-3,3-difluoro-piperidine-2,6-dione

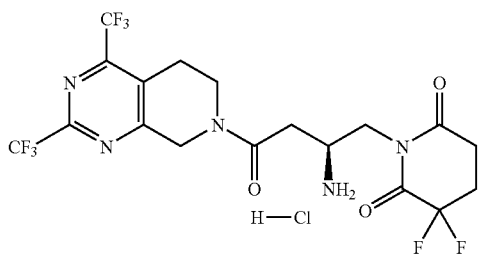

Analogously to the procedure of Example 3, 6.4 mg (yield: 97%) of the title compound was obtained using the compound synthesized in Preparation Example 15.
$^1$H NMR (500 MHz, MeOH-d$_4$) δ2.51-2.54 (m, 2H), 2.85-2.91 (m, 4H), 3.12-3.21 (m, 3H), 4.10-4.20 (m, 4H), 4.95 (m, 2H); MS (m/e) 504 (M+1)

PREPARATION EXAMPLE 16

Synthesis of 3-fluoro-piperidine-2,6-dione (1) Synthesis of 2-fluoro-pentanedioic acid diethyl ester Analogously to the procedure of Preparation Example 3-(1), 1.86 g (yield: 30%) of the title compound was obtained using commercially available bromofluoroacetic acid ethyl ester (7.1 mL, 60 mmol) and ethyl acrylate (3.3 mL, 30 mmol).
$^1$H NMR (400 MHz, CDCl$_3$) δ1.25-1.37 (m, 6H), 2.17-2.37 (m, 2H), 2.51-2.57 (m, 2H), 4.14-4.33 (m, 4H), 4.93-5.08 (m, 1H)

(2) Synthesis of 4-carbamoyl-4-fluoro-butyric acid ethyl ester

Analogously to the procedure of Preparation Example 3-(2), 2.2 g of the crude title compound was obtained using 2-fluoro-pentanedioic acid diethyl ester (2.4 g, 11.7 mmol) synthesized in Section (1).
$^1$H NMR (400 MHz, CDCl$_3$) δ1.21-1.33 (m, 3H), 2.13-2.38 (m, 2H), 2.47-2.52 (m, 2H), 4.13-4.18 (m, 2H), 4.89-5.08 (m, 1H), 5.90-6.32 (b, 1H)

(3) Synthesis of 3-fluoro-piperidine-2,6-dione

Analogously to the procedure of Preparation Example 3-(3), 720 mg (yield: 44%) of the title compound was obtained using 4-carbamoyl-4-fluoro-butyric acid ethyl ester (2.2 g, 12.5 mmol) synthesized in Section (2).
$^1$H NMR (400 MHz, MeOH-d$_4$) δ2.18-2.41 (m, 2H), 2.71-2.75 (m; 2H), 5.11-5.27 (m, 1H); MS (m/e) 132 (M+1)

PREPARATION EXAMPLE 17

Synthesis of (S)-3-t-butoxycarbonylamino-4-(3-fluoro-2-hydroxy-6-oxo-piperidin-1-yl)-butyric acid (1) Synthesis of (S)-3-t-butoxycarbonylamino-4-(3-fluoro-2,6-dioxo-piperidin-1-yl)-butyric acid isopropyl ester Analogously to the procedure of Preparation Example 4-(2), 139 mg of the crude title compound was obtained using 3-fluoro-piperidine-2,6-dione (47 mg, 0.36 mmol) synthesized in Preparation Example 16 and (3S)-t-butoxycarbonylamino-4-hydroxy butyric acid i-propyl ester (78.4 mg, 0.3 mmol) synthesized in Preparation Example 4-(1).
$^1$H NMR (400 MHz, CDCl$_3$) δ1.24-1.39 (m, 6H), 1.44 (s, 9H), 2.24-2.35 (m, 2H), 2.48-2.71 (m, 2H), 2.85-2.91 (m, 2H), 3.73 (d, 1H, J=4.8Hz), 4.09-4.20 (m, 2H), 4.99-5.31 (m, 3H); MS (m/e) 397 (M+Na)

(2) Synthesis of (S)-3-t-butoxycarbonylamino-4-(3-fluoro-2-hydroxy-6-oxo-piperidin-1-yl)-butyric acid isopropyl ester Analogously to the procedure of Preparation Example 4-(3), 109 mg (yield: 78%) of the title compound was obtained using (S)-3-t-butoxycarbonylamino-4-(3-fluoro-2,6-dioxo-piperidin-1-yl)-butyric acid isopropyl ester (139 mg, 0.37 mmol) synthesized in Section (1).
MS (m/e) 399 (M+Na)

(3) Synthesis of (S)-3-t-butoxycarbonylamino-4-(3-fluoro-2-hydroxy-6-oxo-piperidin-1-yl)-butyric acid Analogously to the procedure of Preparation Example 4-(4), 54 mg (yield: 60%) of the title compound was obtained using (S)-3-t-butoxycarbonylamino-4-(3-fluoro-2-hydroxy-6-oxo-piperidin-1-yl)-butyric acid isopropyl ester (102 mg, 0.27 mmol) synthesized in Section (2).
MS (m/e) 357 (M+Na)

PREPARATION EXAMPLE 18

Synthesis of [(S)-3-(2-t-butyl-4-trifluoromethyl-5,8-dihydro-6H-pyrido[3,4-d]pyrimidin-7-yl)-1-(3-fluoro-2-hydroxy-6-oxo-piperidin-1-ylmethyl)-3-oxo-propyl]-carbamic acid t-butyl ester Analogously to the procedure of Preparation Example 6, 42 mg (yield: 65%) of the title compound was obtained using (S)-3-t-butoxycarbonylamino-4-(3-fluoro-2-hydroxy-6-oxo-piperidin-1-yl)-butyric acid (38 mg, 0.11 mmol) synthesized in Preparation Example 17 and 2-t-butyl-4-trifluoromethyl-5,6,7,8-tetrahydro-pyrido[3,4-d]pyrimidine hydrochloride (49 mg, 0.16 mmol) synthesized in Preparation Example 2-(2).
¹H NMR (400 MHz, MeOH-d₄) δ1.41 (d, 18H), 2.17 (m, 2H), 2.45 (m, 2H), 2.71 (m, 2H), 3.00 (m, 1H), 3.11 (m, 2H), 3.92 (m, 3H), 4.11 (m, 1H), 4.88-4.91 (m, 3H) 5.43-5.55 (m, 1H); MS (m/e) 598 (M+Na)

EXAMPLE 16

Synthesis of 1[(S)-2-amino-4-(2-t-butyl-4-trifluoromethyl-5,8-dihydro-6H-pyrido[3,4-d]pyrimidin-7-yl)-4-oxo-butyl]-5-fluoro-6-hydroxy-piperidin-2-one hydrochloride

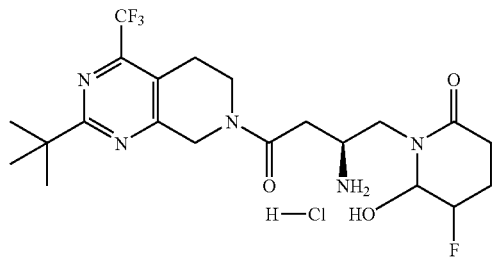

Analogously to the procedure of Example 3, 6.0 mg (yield: 18%) of the title compound was obtained using the compound synthesized in Preparation Example 18.
¹H NMR (400 MHz, MeOH-d₄) δ1.42 (s, 9H), 2.00-2.50 (m, 4H), 2.81-3.11 (m, 5H), 3.50-3.93 (m, 4H), 4.84-5.10 (m, 3H) 5.48-5.62 (m, 1H); MS (m/e) 476 (M+1)

PREPARATION EXAMPLE 19

Synthesis of [(S)-1-(3-fluoro-2-hydroxy-6-oxo-piperidin-1-ylmethyl)-3-(2-furan-2-yl-4-trifluoromethyl-5,8-dihydro-6H-pyrido[3,4-d]pyrimidin-7-yl)-3-oxo-propyl]-carbamic acid t-butyl ester Analogously to the procedure of Preparation Example 6, 49 mg (yield: 79%) of the title compound was obtained using (S)-3-t-butoxycarbonylamino-4-(3-fluoro-2-hydroxy-6-oxo-piperidin-1-yl)-butyric acid (35 mg, 0.11 mmol) synthesized in Preparation Example 17 and 2-furan-2-yl-4-trifluoromethyl-5,6,7,8-tetrahydro-pyrido[3,4-d]pyrimidine hydrochloride (45 mg, 0.15 mmol) synthesized in Preparation Example 2-(5).
MS (m/e) 608 (M+Na)

EXAMPLE 17

Synthesis of 1-[(S)-2-amino-4-(2-furan-2-yl-4-trifluoromethyl-5,8-dihydro-6H-pyrido[3,4-d]pyrimidin-7-yl)-4-oxo-butyl]-5-fluoro-6-hydroxy-piperidin-2-one hydrochloride

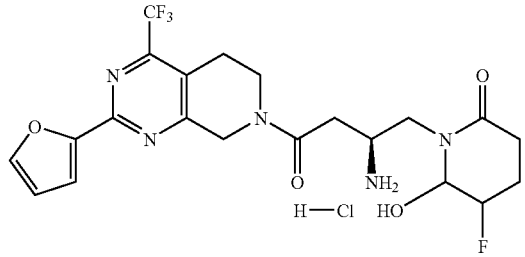

Analogously to the procedure of Example 3, 15 mg (yield: 35%) of the title compound was obtained using the compound synthesized in Preparation Example 19.
¹H NMR (400 MHz, MeOH-d₄) δ2.17-3.14 (m, 9H), 3.70-3.89 (m, 4H), 4.86-4.87 (m, 3H) 5.43-5.55 (m, 1H), 6.68 (m, 1H), 7.41 (m, 1H), 7.79 (m, 1H); MS (m/e) (M+1)

PREPARATION EXAMPLE 20

Synthesis of [(S)-1-(3-fluoro-2-hydroxy-6-oxo-piperidin-1-ylmethyl)-3-oxo-3-(2-thiophen-3-yl-4-trifluoromethyl-5,8-dihydro-6H-pyrido[3,4-d]pyrimidin-7-yl)-propyl]-carbamic acid t-butyl ester Analogously to the procedure of Preparation Example 6, 13 mg (yield: 15%) of the title compound was obtained using (S)-3-t-butoxycarbonylamino-4-(3-fluoro-2-hydroxy-6-oxo-piperidin-1-yl)-butyric acid (48 mg, 0.14 mmol) synthesized in Preparation Example 17 and 2-thiophen-3-yl-4-trifluoromethyl-5,6,7,8-tetrahydro-pyrido[3,4-d]pyrimidine hydrochloride (65 mg, 0.20 mmol) synthesized in Preparation Example 2-(7).
MS (m/e) 624 (M+Na)

EXAMPLE 18

Synthesis of 1-[(S)-2-amino-4-oxo-4-(2-thiophen-3-yl-4-trifluoromethyl-5,8-dihydro-6H-pyrido[3,4-d]pyrimidin-7-yl)-butyl]-5-fluoro-6-hydroxy-piperidin-2-one hydrochloride

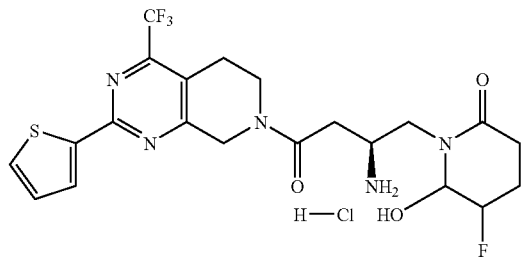

Analogously to the procedure of Example 3, 1.4 mg (yield: 12%) of the title compound was obtained using, the compound synthesized in Preparation Example 20.

¹H NMR (400 MHz, MeOH-d₄) δ2.2-2.3 (m, 4H), 2.50 (m, 1H), 3.00-3.15 (m, 4H), 3.74 (m, 1H), 3.88 (m, 3H), 4.88 (m, 3H), 5.51 (m, 1H), 7.53 (m, 1H), 7.88 (m, 1H), 8.39 (m, 1H); MS (m/e) 502 (M+1)

PREPARATION EXAMPLE 21

Synthesis of [(S)-1-(3-fluoro-2-hydroxy-6-oxo-piperidin-1-ylmethyl)-3-oxo-3-(2-propyl-5-trifluoromethyl-5,8-dihydro-6H-pyrido[3,4-d]pyrimidin-7-yl)-propyl]-carbamic acid t-butyl ester Analogously to the procedure of Preparation Example 6, 15 mg (yield: 18%) of the title compound was obtained using (S)-3-t-butoxycarbonylamino-4-(3-fluoro-2-hydroxy-6-oxo-piperidin-1-yl)-butyric acid (47 mg, 0.14 mmol) synthesized in Preparation Example 17 and 2-propyl-4-trifluoromethyl-5,6,7,8-tetrahydropyrido[3,4-d]pyrimidine hydrochloride (56 mg, 0.20 mmol) synthesized in Preparation Example 2-(1).
MS (m/e) 584 (M+Na)

EXAMPLE 19

Synthesis of 1-[(S)-2-amino-4-oxo-4-(2-propyl-5-trifluoromethyl-5,8-dihydro-6H-pyrido[3,4-d]pyrimidin-7-yl)-butyl]-5-fluoro-6-hydroxy-piperidin-2-one hydrochloride

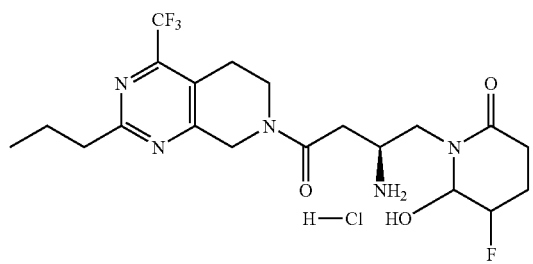

Analogously to the procedure of Example 3, 2.3 mg (yield: 18%) of the title compound was obtained using the compound synthesized in Preparation Example 21.
¹H NMR (400 MHz, MeOH-d₄) δ0.95-0.99 (m, 3H), 1.82-1.84 (m, 2H), 2.18 (m, 2H), 2.44-2.56 (m, 3H), 2.74 (m, 1H), 2.90-3.07 (m, 5H), 3.76-3.89 (m, 4H), 4.84 (m, 3H), 5.54 (m, 1H); MS (m/e) 462 (M+1)

PREPARATION EXAMPLE 22

Synthesis of [(S)-1-(3-fluoro-2-hydroxy-6-oxo-piperidin-1-ylmethyl)-3-oxo-3-(2-pyridin-4-yl-5-trifluoromethyl-5,8-dihydro-6H-pyrido[3,4-d]pyrimidin-7-yl)-propyl]-carbamic acid t-butyl ester Analogously to the procedure of Preparation Example 6, 55 mg (yield: 65%) of the title compound was obtained using (S)-3-t-butoxycarbonylamino-4-(3-fluoro-2-hydroxy-6-oxo-piperidin-1-yl)-butyric acid (33 mg, 0.10 mmol) synthesized in Preparation Example 17 and 2-pyridin-4-yl-4-trifluoromethyl-5,6,7,8-tetrahydro-pyrido[3,4-d]pyrimidine hydrochloride (44 mg, 0.14 mmol) synthesized in Preparation Example 2-(4).
MS (m/e) 619 (M+Na)

EXAMPLE 20

Synthesis of 1-[(S)-2-amino-4-oxo-4-(2-pyridin-4-yl-5-trifluoromethyl-5,8-dihydro-6H-pyrido[3,4-d]pyrimidin-7-yl)-butyl]-5-fluoro-6-hydroxy-piperidin-2-one hydrochloride

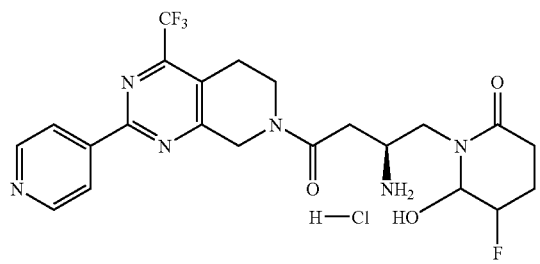

Analogously to the procedure of Example 3, 12 mg (yield: 24%) of the title compound was obtained using the compound synthesized in Preparation Example 22.
¹H NMR (400 MHz, MeOH-d₄) δ1.30-3.21 (m, 8H), 3.37-4.20 (m, 5H), 5.00 (m, 3H), 8.43 (s, 2H), 8.76 (s, 2H); MS (m/e) 519 (M+Na)

PREPARATION EXAMPLE 23

Synthesis of 3-methyl-piperidine-2,6-dione

Acetic anhydride was added to commercially available 2-methylglutaric acid (1 g, 6.8 mmol) at room temperature, and the mixture was stirred at 60° C. for 8 hours under reflux. After completion of the reaction was confirmed by TLC, the remaining acetic anhydride was removed under reduced pressure. The concentrated compound was dissolved in tetrahydrofuran and an ammonia aqueous solution (1.7 mL, 14.6 mmol) was slowly added thereto at 0° C., followed by stirring for 8 hours at room temperature. After the reaction was complete, the remaining ammonia aqueous solution was removed under reduced pressure and an acetic anhydride was added, followed by reflux at 60° C. for 8 hours. The residual acetic anhydride was removed under reduced pressure. The concentrate was purified by column chromatography (ethyl acetate:hexane=1:1) to afford 682 mg (yield: 78%) of the title compound.
¹H NMR (400 MHz, MeOH-d₄) δ1.24-1.28 (m, 3H), 1.71-1.77 (1H), 2.04-2.08 (m, 1H), 2.57-2.65 (m 3H); MS (m/e) 128 (M+1)

PREPARATION EXAMPLE 24

Synthesis of (S)-3-t-butoxycarbonylamino-4-(3-methyl-2,6-dioxo-piperidin-1-yl)-butyric acid (1) Synthesis of (S)-3-t-butoxycarbonylamino-4-(3-methyl-2,6-dioxo-piperidin-1-yl)-butyric acid benzyl ester Analogously to the procedure of Preparation Example 4-(2), 129 mg (yield: 88%) of the title compound was obtained using 3-methyl-piperidine-2,6-dione (53 mg, 0.42 mmol) synthesized in Preparation Example 23 and (S)-3-t-butoxycarbonylamino-4-hydroxy-butyric acid benzyl ester (107 mg, 0.35 mmol) synthesized in Preparation Example 14-(1).

¹H NMR (400 MHz, CDCl₃) δ1.30-1.35 (m, 3H), 1.47 (s, 9H), 1.78-2.01 (m, 2H), 2.53-2.85 (m, 5H), 3.72 (m, 1H), 4.13-4.36 (m, 2H), 5.12-5.23 (m, 3H), 7.30-7.39 (m, 5H) MS (m/e) 441 (M+Na)

(2) Synthesis of (S)-3-t-butoxycarbonylamino-4-(3-methyl-2,6-dioxo-piperidin-1-yl)-butyric acid (S)-3-t-butoxycarbonylamino-4-(3-methyl-2,6-dioxo-piperidin-1-yl)-butyric acid benzyl ester (218 mg, 0.52 mmol) synthesized in Section (1) was dissolved in methanol and 10% Pd/C (22 mg, 0.1 eq) was added thereto, followed by stirring for 1 hour under 1 atm hydrogen gas. After the reaction was complete, Pd on charcoal was removed by celite filtration. The residue was purified by prep-TLC to afford 59 mg (yield: 35%) of the title compound.
¹H NMR (400 MHz, MeOH-d₄) δ1.28 (m, 3H), 1.42 (s, 9H), 1.80-1.99 (m, 2H), 2.38-2.87 (m, 5H), 3.72 (m, 1H), 4.22-4.44 (m, 2H); MS (m/e) 351 (M+Na)

PREPARATION EXAMPLE 25

Synthesis of [(S)-1-(3-methyl-2,6-dioxo-piperidin-1-ylmethyl)-3-oxo-3-(2-thiophen-3-yl-4-trifluoromethyl-5,8-dihydro-6H-pyrido[3,4-d]pyrimidin-7-yl)-propyl]-carbamic acid t-butyl ester Analogously to the procedure of Preparation Example 6, 47 mg (yield: 88%) of the title compound was obtained using (S)-3-t-butoxycarbonylamino-4-(3-methyl-2,6-dioxo-piperidin-1-yl)-butyric acid (29 mg, 0.09 mmol) synthesized in Preparation Example 24 and 2-thiophen-3-yl-4-trifluoromethyl-5,6,7,8-tetrahydro-pyrido[3,4-d]pyrimidine hydrochloride (40 mg, 0.12 mmol) synthesized in Preparation Example 2-(7).
¹H NMR (400 MHz, MeOH-d₄) δ1.24-1.28 (m, 3H), 1.38 (s, 9H), 1.68-2.04 (m, 2H), 2.69-2.94 (m, 5H), 3.02-3.17 (m, 2H), 3.91 (m, 2H), 3.72 (m, 1H), 4.11-4.20 (m, 3H), 4.80-4.90 (m, 2H), 7.53 (m, 1H), 7.91 (m, 1H), 8.41(m, 1H); MS (m/e) 618 (M+Na)

EXAMPLE 21

Synthesis of 1-[(S)-2-amino-4-oxo-4-(2-thiophen-3-yl-4-trifluoromethyl-5,8-dihydro-6H-pyrido[3,4-d]pyrimidin-7-yl)-butyl]-3-methyl-piperidine-2,6-dione hydrochloride

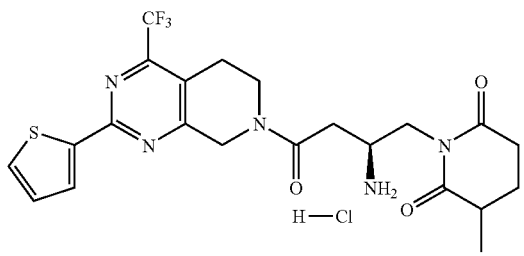

Analogously to the procedure of Example 3, 23 mg (yield: 65%) of the title compound was obtained using the compound synthesized in Preparation Example 25.
¹H NMR (400 MHz, MeOH-d₄) δ1.23-1.31 (m, 3H), 1.72-2.17 (m, 2H), 2.64-2.72 (m, 5H), 3.04-3.1.3 (m, 2H), 3.55-3.68 (m, 2H), 3.87-3.93 (m, 2H), 4.17 (m, 1H), 4.90 (m, 2H), 7.53 (m, 1H), 7.90 (m, 1H), 8.41(m, 1H); MS (m/e) 496 (M+1)

PREPARATION EXAMPLE 26

Synthesis of 3-methyl-pyrrolidine-2,5-dione (1) Synthesis of 2-methyl-succinic acid Commercially available dimethyl methylsuccinate (1.57 g, 9.8 mmol) was dissolved in a 3:1 mixed solvent of tetrahydrofuran and water, and lithium hydroxide (4 g, 98 mmol) was added and stirred for 2 days at 40° C. under reflux. After completion of the reaction was confirmed by TLC, the residue was distilled under reduced pressure to afford the title compound.
¹H NMR (400 MHz, MeOH-d₄) δ1.21-1.23 (d, 3H, J=7.2Hz), 2.43-2.48 (m, 1H), 2.64-2.70 (m, 1H), 2.80-2.89 (m, 1H)

(2) Synthesis of 3-methyl-pyrrolidine-2,5-dione

Analogously to the procedure of Preparation Example 23, 250 mg of the title compound was obtained using 2-methyl-succinic acid synthesized in Section (1).
¹H NMR (400 MHz, MeOH-d₄) δ1.19-1.29 (m, 3H), 2.32-2.40 (m, 1H), 2.71-2.96 (m, 2H)

PREPARATION EXAMPLE 27

Synthesis of (S)-3-t-butoxycarbonylamino-4-(3-methyl-2,5-dioxo-pyrrolidin-1-yl)-butyric acid (1) Synthesis of (S)-3-t-butoxycarbonylamino-4-(3-methyl-2,5-dioxo-pyrrolidin-1-yl)-butyric acid benzyl ester Analogously to the procedure of Preparation Example 4-(2), 230 mg of the crude title compound was obtained using 3-methyl-pyrrolidine-2,5-dione (61 mg, 0.54 mmol) synthesized in Preparation Example 26 and (S)-3-t-butoxycarbonylamino-4-hydroxy-butyric acid benzyl ester (140 mg, 0.45 mmol) synthesized in Preparation Example 14-(1).
¹H NMR (400 MHz, CDCl₃) δ1.31-1.39 (m, 3H), 1.43 (s, 9H), 2.29-2.39 (m, 1H), 2.62-2.92 (m, 4H), 3.70 (m, 1H), 4.18 (m, 2H), 5.13-5.14 (m, 2H), 5.24 (b, 1H), 7.35-7.36 (m, 5H); MS (m/e) 427 (M+Na)

(2) Synthesis of (S)-3-t-butoxycarbonylamino-4-(3-methyl-2,5-dioxo-pyrrolidin-1-yl)-butyric acid Analogously to the procedure of Preparation Example 23-(2), 62 mg of the title compound was obtained using (S)-3-t-butoxycarbonylamino-4-(3-methyl-2,5-dioxo-pyrrolidin-1-yl)-butyric acid benzyl ester (218 mg, 0.52 mmol) synthesized in Section (1).
MS (m/e) 337 (M+Na)

PREPARATION EXAMPLE 28

Synthesis of [(S)-3-(2-t-butyl-4-trifluoromethyl-5,8-dihydro-6H-pyrido[3,4-d]pyrimidin-7-yl)-1-(3-methyl-2,5-dioxo-pyrrolidin-1-ylmethyl)-3-oxo-propyl]-carbamic acid t-butyl ester Analogously to the procedure of Preparation Example 6, 74 mg of the title compound was quantitatively obtained using (S)-3-t-butoxycarbonylamino-4-(3-methyl-2,5-dioxo-pyrrolidin-1-yl)-butyric acid (39 mg, 0.13 mmol) synthesized in Preparation Example 27 and 2-t-butyl-4-trifluoromethyl-5,6,7,8-tetrahydro-pyrido[3,4-d]pyrimidine hydrochloride (52 mg, 0.18 mmol) synthesized in Preparation Example 2-(2).

$^1$H NMR (400 MHz, MeOH-d$_4$) δ1.24-1.28 (m, 3H), 1.38-1.42 (m, 18H), 2.27-2.92 (m, 5H), 3.00-3.12 (m, 2H), 3.63-4.59 (m, 5H), 4.82-4.86 (m, 2H); MS (m/e) 578 (M+Na)

EXAMPLE 22

Synthesis of 1-[(S)-2-amino-4-(2-t-butyl-4-trifluoromethyl-5,8-dihydro-6H-pyrido[3,4-d]pyrimidin-7-yl)-4-oxo-butyl]-3-methyl-pyrrolidine-2,6-dione hydrochloride

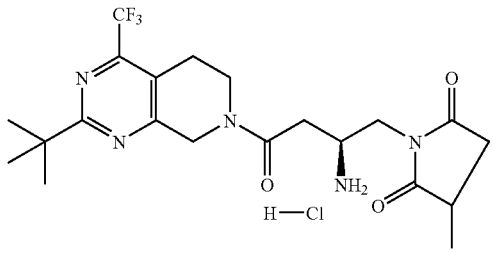

Analogously to the procedure of Example 3, 32 mg (yield: 61%) of the title compound was obtained using the compound synthesized in Preparation Example 28.

$^1$H NMR (400 MHz, MeOH-d$_4$) δ1.26-1.29 (m, 3H), 1.42 (s, 9H), 2.33-2.38 (m, 1H), 2.57-2.67 (m, 2H), 2.90-2.92 (m, 2H), 3.00-3.10 (m, 2H), 3.55-3.37 (m, 3H), 3.84-3.90 (m, 2H), 4.82-4.86 (m, 2H); MS (m/e) 456 (M+1)

EXPERIMENTAL EXAMPLE 1

Assay of DPP-IV Inhibitory Activity

Dipeptidyl peptidase-IV (DPP-IV), known as serine protease, was obtained by a modification of the known method (Tanaka T. et al, Proc. Natl. Acad. Sci. USA, (1994) 91,3082-3086), which comprises cloning, purification by use of Baculovirus and activation steps. DPP-IV was used to test the pharmaceutical efficacy of candidate inhibitors as follows. The cloned DPP-IV was expressed in Baculovirus, which was purified by a nickel column and then subjected to dialysis. The inhibitors synthesized in Examples were tested to determine the DPP-IV inhibitory activity thereof using a fluorescent substrate, Ac-Gly-Pro-AFC. Enzymatic reactions were conducted for various concentrations of inhibitors, using 100 μM Ac-Gly-Pro-AFC at 25° C. in a buffer solution containing 50. mM HEPES (pH 7.4), with the concentration of DPP-IV being 7.1 nM. IC$_{50}$ values of the inhibitors were determined by measuring the amount of fluorescence so emitted in a fluorescence spectrometer after allowing an enzymatic reaction for 1 hour, and then calculating the concentration of inhibitors exhibiting 50% inhibition of the total enzymatic reaction. Spectra MAX GeminiXS fluorescence spectrometer (Molecular Device Co.) was used as the fluorescence spectrometer and the excitation and emission wavelengths were set to 400 nm and 505 nm, respectively. The results obtained are summarized in Table 1 below.

TABLE 1

| | IC$_{50}$ (nM) | | IC$_{50}$ (nM) |
|---|---|---|---|
| Example 1 | 36 | Example 2 | 5 |
| Example 3 | 20 | Example 4 | 39 |
| Example 5 | 17 | Example 6 | 10 |
| Example 7 | 63 | Example 8 | 6 |
| Example 9 | 93 | Example 10 | 14 |
| Example 11 | 160 | Example 12 | 10 |
| Example 13 | 195 | Example 14 | 57 |
| Example 15 | 2500 | Example 16 | 197 |
| Example 17 | 81 | Example 18 | 159 |
| Example 19 | 409 | Example 20 | 206 |
| Example 21 | >2500 | Example 22 | >2500 |

EXPERIMENTAL EXAMPLE 2

Assay of DPP-II, VIII and IX Inhibitory Activity

In order to compare the DPP enzyme selectivity of some compounds of Examples 1 to 22 and known DPP-IV inhibitors, the enzyme inhibitory activity of these test compounds was measured as follows.

Measurement of DPP-II inhibitory activity: DPP-II was obtained and purified. Using Gly-Pro-AFC as the substrate, DPP-IV inhibitors as set forth in Table 2 below were assayed for DPP-II inhibitory activity. Enzymatic reactions were conducted for various concentrations of DPP-IV inhibitors, using 0.018 μg DPP-II and 100 μM Gly-Pro-AFC in a buffer solution containing 50 mM acetic acid (pH 4.5) at room temperature. IC$_{50}$ values of the inhibitors were determined by tracing the reaction rate using a fluorescence spectrometer for 60 min and analyzing the results using TableCurve 2D (v 5.01). DPP-IV inhibitors were analyzed using the fluorescence spectrometer at the excitation and emission wavelengths of 405 nm and 505 nm, respectively.

Measurement of DPP-VIII inhibitory activity: DPP-VIII was obtained and purified. Using Gly-Pro-AFC as the substrate, DPP-IV inhibitors as set forth in Table 2 below were assayed for DPP-VIII inhibitory activity. Enzymatic reactions were conducted for various concentrations of DPP-IV inhibitors, using 0.0049 μg DPP-VIII and 100 μM Gly-Pro-AFC in a buffer solution containing 50 mM HEPES (pH 7.5) at room temperature. IC$_{50}$ values of the inhibitors were determined by tracing the reaction rate using a fluorescence spectrometer for 60 min and analyzing the results using TableCurve 2D (v 5.01). DPP-IV inhibitors were analyzed using the fluorescence spectrometer at the excitation and emission wavelengths of 405 nm and 505 nm, respectively.

Measurement of DPP-IX inhibitory activity: DPP-IX was obtained and purified. Using Gly-Pro-AFC as the substrate, DPP-IV inhibitors as set forth in Table 2 below were assayed for DPP-IX inhibitory activity. Enzymatic reactions were conducted for various concentrations of DPP-IV inhibitors, using 200 ng DPP-IX and 100 μM Gly-Pro-AFC in a buffer solution containing 50 mM HEPES (pH 7.5) at room temperature. IC$_{50}$ values of the inhibitors were determined by time-course tracing of the reaction rate using a fluorescence spectrometer and analyzing the results using TableCurve 2D (v 5.01). DPP-IV inhibitors were analyzed using the fluorescence spectrometer at the excitation and emission wavelengths of 405 nm and 505 nm, respectively.

The assay results obtained are summarized in Table 2 below.

TABLE 2

| Inhibitors | DPP-II (μM) | DPP-IV (nM) | DPP-VIII (μM) | DPP-IX (μM) |
|---|---|---|---|---|
| Example 2 | >400 | 5 | >400 | >400 |
| Example 5 | >161 | 17 | >400 | >400 |
| Example 6 | >70 | 10 | >127 | >100 |
| Example 8 | >80 | 6 | >400 | >130 |
| Example 10 | >400 | 14 | >400 | >210 |
| Example 12 | >50 | 10 | >400 | >110 |
| Example 83[a] | >400 | 18 | 15 | 124 |
| Vildagliptin (Norvatis)[b] | >10 | 62 | >10 | 1.3 |
| Sitagliptin (Merck)[c] | >100 | 18 | 48 | >100 |
| Saxagliptin (BMS) | >400 | 13 | 0.17 | 0.061 |

[a]See WO 06/104356 assigned to the present applicant
[b]Data published in IDF, 2006
[c]Kim, D., et al., J. Med Chem, 2005, 48, 141-451

As can be seen from the results of Table 2, the compounds of the present invention exhibited excellent selectivity for DPP-IV, as compared to DPP-IV inhibitors of WO 06/104356. These results suggest that potential toxicity of the compounds due to side reactions can be minimized as described before.

Industrial Applicability

As apparent from the foregoing, it is clear that novel compounds according to the present invention inhibit DPP-IV activity, thus resulting in facilitation of insulin secretion and consequently lowering of blood glucose levels. Accordingly, these compounds can be used for the treatment or prevention of DPP-IV-related diseases, for example, diabetes (particularly, type II), obesity and the like.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A compound represented by Formula 1:

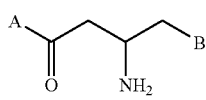

(1)

wherein
A is selected from a substituent of Formula 2:

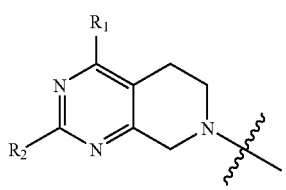

(2)

wherein
$R_1$ is hydrogen or $CF_3$, and
$R_2$ is selected from the group consisting of hydrogen, substituted or unsubstituted $C_1$-$C_{10}$ alkyl, substituted or unsubstituted $C_3$-$C_{10}$ cycloalkyl, substituted or unsubstituted $C_3$-$C_{10}$ heterocycloalkyl, substituted or unsubstituted $C_4$-$C_8$ aryl and substituted or unsubstituted $C_3$-$C_7$ heteroaryl; and a substituent of Formula 3:

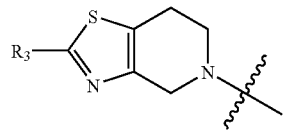

(3)

wherein $R_3$ is selected from the group consisting of hydrogen, halogen, and substituted or unsubstituted $C_1$-$C_4$ alkyl; and B is selected from the group consisting of a substituent of Formula 4:

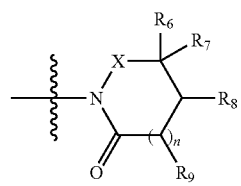

(4)

wherein
X is —$CR_4R_5$— or —CO—, wherein $R_4$ and $R_5$ are each independently hydrogen or hydroxy, provided that at least one of $R_4$ and $R_5$ is hydroxy,
$R_6$, $R_7$, $R_8$ and $R_9$ are each independently selected from the group consisting of hydrogen, halogen and substituted or unsubstituted $C_1$-$C_4$ alkyl, and
n is 0 or 1;

a substituent of Formula 5:

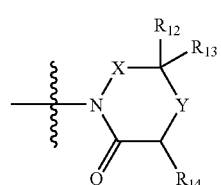

(5)

wherein
X is —$CR_{10}R_{11}$— or —CO—, wherein $R_{10}$ and $R_{11}$ are each independently hydrogen or hydroxy, provided that at least one of $R_{10}$ and $R_{11}$ is hydroxy,
$R_{12}$, $R_{13}$ and $R_{14}$ are each independently selected from the group consisting of hydrogen, halogen and substituted or unsubstituted $C_1$-$C_4$ alkyl, and
Y is oxygen or sulfur;

a substituent of Formula 6:

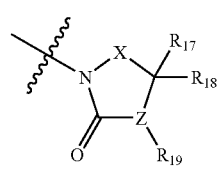

(6)

wherein
X is —$CR_{15}R_{16}$— or —CO—, wherein $R_{15}$ and $R_{16}$ are each independently hydrogen or hydroxy, provided that at least one of $R_{15}$ and $R_{16}$ is hydroxy, Z is —CH— or oxygen, provided that when Z is oxygen, $R_{19}$ is absent, and $R_{17}$, $R_{18}$ and $R_{19}$ are each independently selected from the group consisting of hydrogen, halogen, and substituted or unsubstituted $C_1$-$C_4$ alkyl; and a substituent of Formula 7:

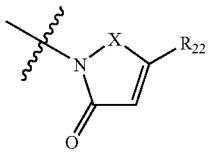

(7)

wherein

X is —$CR_{20}R_{21}$— or —CO—, wherein $R_{20}$ and $R_{21}$ are each independently hydrogen or hydroxy, provided that at least one of $R_{20}$ and $R_{21}$ is hydroxy, and $R_{22}$ is substituted or unsubstituted $C_1$-$C_4$ alkyl; or a pharmaceutically acceptable salt thereof.

2. The compound according to claim 1, wherein when the alkyl, cycloalkyl, heterocycloalkyl, aryl or heteroaryl is substituted, the substituent is $C_1$-$C_{10}$ alkyl or halogen.

3. The compound according to claim 2, wherein the halogen is fluorine.

4. The compound according to claim 1, wherein A in Formula 1 is a substituent represented by Formula 2 wherein $R_1$ is hydrogen or $CF_3$, and $R_2$ is selected from the group consisting of hydrogen, and $C_1$-$C_5$ alkyl, $C_3$-$C_6$ cycloalkyl, $C_3$-$C_{10}$ heterocycloalkyl, $C_4$-$C_8$ aryl and $C_3$-$C_7$ heteroaryl, each of which is optionally substituted by halogen.

5. The compound according to claim 4, wherein when $R_2$ is unsubstituted or halogen-substituted $C_3$-$C_{10}$ heterocycloalkyl or unsubstituted or halogen-substituted $C_3$-$C_7$ heteroaryl, the heterocycloalkyl or heteroaryl is any one selected from the group consisting of furan, thiophene, pyrrole, pyrrolidine, imidazole, pyrazole, pyrazoline, oxazole, oxazoline, isoxazole, isoxazoline, thiazole, thiazoline, isothiazole, isothiazolidine, thiadiazole, thiadiazoline, tetrahydrofuran, tetrahydrothiophene, imidazolidine, pyrazolidine, oxazolidine, isoxazolidine, thiazolidine, isothiazolidine, thiadiazolidine, sulfolane, pyran, dihydropyran, tetrahydropyran, pyridine, pyridinone, pyridazine, pyrazine, pyrimidine, piperidine, piperazine, morpholine, pyridazinone, tetrazole, triazole, triazolidine and azepine.

6. The compound according to claim 4, wherein $R_2$ is selected from the group consisting of trifluoromethyl, propyl, butyl, t-butyl, cyclobutyl, pyridine, furan, methoxyethyl, thiophene and 4-fluorophenyl.

7. The compound according to claim 1, wherein B in Formula 1 is a substituent represented by Formula 4 wherein X is —(CH—OH)— or —CO—, $R_6$ and $R_7$ are each independently selected from the group consisting of hydrogen, fluoro and unsubstituted $C_1$-$C_4$ alkyl, and $R_8$ and $R_9$ are each independently hydrogen.

8. The compound according to claim 1, wherein the compound is a compound of Formula 1a:

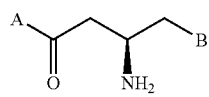

(1a)

wherein A and B are as defined for Formula 1.

9. The compound according to claim 1, wherein the compound is any one of the following compounds:
1-[(2S)-amino-4-(2,4-bis-trifluoromethyl-5,8-dihydro-6H-pyrido[3,4-d]pyrimidin-7-yl)-4-oxo-butyl]-5,5-difluoro-(6R)-hydroxy-piperidin-2-one,
1-[(2S)-amino-4-(2,4-bis-trifluoromethyl-5,8-dihydro-6H-pyrido[3,4-d]pyrimidin-7-yl)-4-oxo-butyl]-5,5-difluoro-(6S)-hydroxy-piperidin-2-one,
1-[(S)-2-amino-4-oxo-4-(2-propyl-4-trifluoromethyl-5,8-dihydro-6H-pyrido[3,4-d]pyrimidin-7-yl)-butyl]-5,5-difluoro-6-hydroxy-piperidin-2-one,
1-[(S)-2-amino-4-(2-t-butyl-4-trifluoromethyl-5,8-dihydro-6H-pyrido[3,4-d]pyrimidin-7-yl)-4-oxo-butyl]-5,5-difluoro-6-hydroxy-piperidin-2-one,
1-[(S)-2-amino-4-(2-cyclobutyl-4-trifluoromethyl-5,8-dihydro-6H-pyrido[3,4-d]pyrimidin-7-yl)-4-oxo-butyl]-5,5-difluoro-6-hydroxy-piperidin-2-one,
1-[(S)-2-amino-4-oxo-4-(2-pyridin-4-yl-4-trifluoromethyl-5,8-dihydro-6H-pyrido[3,4-d]pyrimidin-7-yl)-butyl]-5,5-difluoro-6-hydroxy-piperidin-2-one,
1-[(S)-2-amino-4-(2-furan-2-yl-4-trifluoromethyl-5,8-dihydro-6H-pyrido[3,4-d]pyrimidin-7-yl)-butyl]-4-oxo-butyl]-5,5-difluoro-6-hydroxy-piperidin-2-one,
1-{(S)-2-amino-4-[2-(2-methoxy-ethyl)-4-trifluoromethyl-5,8-dihydro-6H-pyrido[3,4-d]pyrimidin-7-yl]-4-oxo-butyl}-5,5-difluoro-6-hydroxy-piperidin-2-one,
1-[(S)-2-amino-4-oxo-4-(2-thiophen-3-yl-4-trifluoromethyl-5,8-dihydro-6H-pyrido[3,4-d]pyrimidin-7-yl)-butyl]-5,5-difluoro-6-hydroxy-piperidin-2-one,
1-{(S)-2-amino-4-[2-(4-fluoro-phenyl)-4-trifluoromethyl-5,8-dihydro-6H-pyrido[3,4-d]pyrimidin-7-yl]-4-oxo-butyl}-5,5-difluoro-6-hydroxy-piperidin-2-one,
1-[(S)-2-amino-4-(2,4-bis-trifluoromethyl-5,8-dihydro-6H-pyrido[3,4-d]pyrimidin-7-yl)-4-oxo-butyl]-3,3-difluoro-piperidine-2,6-dione,
1-[(S)-2-amino-4-(2-t-butyl-4-trifluoromethyl-5,8-dihydro-6H-pyrido[3,4-d]pyrimidin-7-yl)-4-oxo-butyl]-5-fluoro-6-hydroxy-piperidin-2-one,
1-[(S)-2-amino-4-(2-furan-2-yl-4-trifluoromethyl-5,8-dihydro-6H-pyrido[3,4-d]pyrimidin-7-yl)-4-oxo-butyl]-5-fluoro-6-hydroxy-piperidin-2-one,
1-[(S)-2-amino-4-oxo-4-(2-thiophen-3-yl-4-trifluoromethyl-5,8-dihydro-6H-pyrido[3,4-d]pyrimidin-7-yl)-butyl]-5-fluoro-6-hydroxy-piperidin-2-one,
1-[(S)-2-amino-4-oxo-4-(2-propyl-5-trifluoromethyl-5,8-dihydro-6H-pyrido[3,4-d]pyrimidin-7-yl)-butyl]-5-fluoro-6-hydroxy-piperidin-2-one,
1-[(S)-2-amino-4-oxo-4-(2-pyridin-4-yl-5-trifluoromethyl-5,8-dihydro-6H-pyrido[3,4-d]pyrimidin-7-yl)-butyl]-5-fluoro-6-hydroxy-piperidin-2-one,
1-[(S)-2-amino-4-oxo-4-(2-thiophen-3-yl-4-trifluoromethyl-5,8-dihydro-6H-pyrido[3,4-d]pyrimidin-7-yl)-butyl]-3-methyl-piperidine-2,6-dione, and
1-[(S)-2-amino-4-(2-t-butyl-4-trifluoromethyl-5,8-dihydro-6H-pyrido[3,4-d]pyrimidin-7-yl)-4-oxo-butyl]-3-methyl-pyrrolidine-2,6-dione.

10. A pharmaceutical composition for inhibiting dipeptidyl peptidase-IV (DPP-IV) comprising a compound of Formula 1 of claim 1, or a pharmaceutically acceptable salt thereof; and a pharmaceutically acceptable carrier, diluent or excipient, or any combination thereof.

11. The pharmaceutical composition according to claim 10, wherein the pharmaceutical composition is formulated for treating a DPP-IV-related disease.

12. The pharmaceutical composition according to claim 11, wherein the DPP-IV-related disease is diabetes or obesity.

* * * * *